US011147927B2

(12) United States Patent
Hochman et al.

(10) Patent No.: US 11,147,927 B2
(45) Date of Patent: *Oct. 19, 2021

(54) DEVICE AND METHOD FOR IDENTIFICATION OF A TARGET REGION

(71) Applicant: Milestone Scientific, Inc., Roseland, NJ (US)

(72) Inventors: Mark N. Hochman, Lake Success, NY (US); Richard K. Buck, Crystal Lake, IL (US); Leonard A. Osser, Roseland, NJ (US)

(73) Assignee: Milestone Scientific, Inc., Roseland, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/163,822

(22) Filed: Feb. 1, 2021

(65) Prior Publication Data

US 2021/0170110 A1      Jun. 10, 2021

Related U.S. Application Data

(63) Continuation of application No. 17/096,411, filed on Nov. 12, 2020, now Pat. No. 10,960,141, which is a
(Continued)

(51) Int. Cl.
*A61M 5/20* (2006.01)
*A61M 5/48* (2006.01)
(Continued)

(52) U.S. Cl.
CPC .......... *A61M 5/31573* (2013.01); *A61M 5/20* (2013.01); *A61M 5/3129* (2013.01);
(Continued)

(58) Field of Classification Search
CPC .......... A61M 5/16836; A61M 5/16859; A61M 5/1723; A61M 5/48; A61M 2005/31588;
(Continued)

(56) References Cited

U.S. PATENT DOCUMENTS 3,867,934 A    2/1975  Ollivier
4,356,826 A   11/1982  Kubota
(Continued)

FOREIGN PATENT DOCUMENTS

DE    202005019430    2/2006
EP       0303824      2/1989
(Continued)

OTHER PUBLICATIONS

International Search Report and Written Opinion issued in International Application No. PCT/US16/57264 dated Mar. 22, 2017.
(Continued)

*Primary Examiner* — Nathan R Price
*Assistant Examiner* — Justin L Zamory
(74) *Attorney, Agent, or Firm* — Niels Haun; Dann, Dorfman, Herrell & Skillman, P.C.

(57) ABSTRACT

A method and apparatus are provided for use in locating a target region which is situated in the body of a subject, for example for the delivery of drugs. The system includes an assembly for controlling the flow of fluid from a fluid reservoir to a conduit, such as a needle. A sensor detects a characteristic indicative of the fluid pressure in the conduit. The system processes data from the sensor to detect the presence of a pulsatile waveform. A controller may control further operation of the system based on information regarding the presence of the pulsatile waveform and features of the waveform, such as amplitude.

7 Claims, 8 Drawing Sheets

Related U.S. Application Data continuation of application No. PCT/US2020/022910, filed on Mar. 16, 2020, now abandoned, which is a continuation of application No. 16/414,499, filed on May 16, 2019, now Pat. No. 10,646,660.

(51) Int. Cl.
*A61M 5/315* (2006.01)
*A61M 5/31* (2006.01)
*A61M 25/06* (2006.01)

(52) U.S. Cl.
CPC .......... *A61M 5/31576* (2013.01); *A61M 5/48* (2013.01); *A61M 25/065* (2013.01); *A61M 2005/31588* (2013.01); *A61M 2205/3331* (2013.01)

(58) Field of Classification Search
CPC ........... A61M 2005/16863; A61M 2205/3344; A61M 2205/332; A61M 2205/3331; A61M 1/3663; A61B 5/02108; A61B 5/0215
See application file for complete search history.

(56) References Cited

U.S. PATENT DOCUMENTS

| | | | |
|---|---|---|---|
| 4,403,988 A | 9/1983 | Binard | |
| 4,518,383 A | 5/1985 | Evans | |
| 4,624,659 A | 11/1986 | Goldberg | |
| 4,679,567 A | 7/1987 | Hanlon | |
| 4,790,821 A | 12/1988 | Stines | |
| 4,801,293 A | 1/1989 | Jackson | |
| 4,893,630 A | 1/1990 | Bray, Jr. | |
| 4,988,337 A | 1/1991 | Ito | |
| 4,998,914 A | 3/1991 | West | |
| 5,100,390 A | 3/1992 | Lubeck | |
| 5,178,603 A | 1/1993 | Prince | |
| 5,197,895 A | 3/1993 | Stupecky | |
| 5,267,565 A | 12/1993 | Beard | |
| 5,269,762 A | 12/1993 | Armbruster | |
| 5,295,967 A | 3/1994 | Rondelet | |
| D348,101 S | 6/1994 | Poli | |
| 5,378,231 A | 1/1995 | Johnson | |
| 5,405,269 A | 4/1995 | Stupecky | |
| D360,259 S | 7/1995 | Ijiri | |
| 5,520,650 A | 5/1996 | Zadini | |
| 5,611,778 A | 3/1997 | Brinon | |
| 5,660,567 A | 8/1997 | Nierlich | |
| 5,681,285 A | 10/1997 | Ford | |
| 5,690,618 A | 11/1997 | Smith | |
| D390,654 S | 2/1998 | Alsberg | |
| 5,727,553 A | 3/1998 | Saad | |
| 5,810,770 A | 9/1998 | Chin | |
| D409,148 S | 5/1999 | Yotsutani | |
| 5,902,273 A | 5/1999 | Yang | |
| 5,954,701 A | 9/1999 | Matalon | |
| 6,022,337 A | 2/2000 | Herbst | |
| 6,024,576 A | 2/2000 | Bevirt | |
| 6,120,457 A | 9/2000 | Coombes | |
| 6,126,610 A | 10/2000 | Rich | |
| 6,159,161 A | 12/2000 | Hodosh | |
| D436,927 S | 1/2001 | Hogan | |
| 6,200,289 B1 | 3/2001 | Hochman | |
| 6,241,704 B1 * | 6/2001 | Peterson | F04B 43/082 604/65 |
| 6,468,241 B1 | 10/2002 | Gelfand | |
| 6,520,928 B1 * | 2/2003 | Junior | A61M 5/14546 604/152 |
| 6,569,147 B1 | 5/2003 | Evans | |
| 6,652,482 B2 | 11/2003 | Hochman | |
| 6,695,806 B2 | 2/2004 | Gelfand | |
| 6,705,990 B1 | 3/2004 | Gallant | |
| 6,716,192 B1 | 4/2004 | Orosz, Jr. | |
| 6,773,417 B2 | 8/2004 | Fitzgibbons | |
| 6,786,885 B2 | 9/2004 | Hochman | |
| 6,866,648 B2 | 3/2005 | Hadzic | |
| 6,887,216 B2 | 5/2005 | Hochman | |
| 6,942,637 B2 | 9/2005 | Cartledge | |
| 7,022,072 B2 | 4/2006 | Fox | |
| 7,198,602 B2 | 4/2007 | Eide | |
| 7,285,100 B2 | 10/2007 | Lemaire | |
| D556,910 S | 12/2007 | Reihanifam | |
| 7,335,162 B2 | 2/2008 | Eide | |
| 7,364,570 B2 | 4/2008 | Gerondale | |
| 7,395,214 B2 | 7/2008 | Shillingburg | |
| 7,449,008 B2 | 11/2008 | Hochman | |
| D600,644 S | 9/2009 | Leung | |
| 7,604,602 B2 | 10/2009 | Roteliuk | |
| 7,618,409 B2 | 11/2009 | Hochman | |
| 7,635,338 B2 | 12/2009 | Eide | |
| 7,641,637 B2 | 1/2010 | Gerondale | |
| 7,727,224 B2 | 6/2010 | Hadzic | |
| 7,775,985 B2 | 8/2010 | Eide | |
| D630,727 S | 1/2011 | Petrovic | |
| 7,896,833 B2 | 3/2011 | Hochman | |
| 7,922,689 B2 | 4/2011 | Lechner | |
| D642,984 S | 8/2011 | Sasaki | |
| 8,002,736 B2 | 8/2011 | Patrick | |
| 8,016,763 B2 | 9/2011 | Eide | |
| 8,079,976 B2 | 12/2011 | Patrick | |
| 8,137,312 B2 | 3/2012 | Sundar | |
| 8,142,414 B2 | 3/2012 | Patrick | |
| 8,197,443 B2 | 6/2012 | Sundar | |
| 8,256,984 B2 | 9/2012 | Fathallah | |
| 8,262,584 B2 | 9/2012 | Eide | |
| D669,096 S | 10/2012 | Katsura | |
| D669,165 S | 10/2012 | Estes | |
| 8,282,565 B2 | 10/2012 | Mahapatra | |
| 8,308,654 B2 | 11/2012 | Eide | |
| 8,398,564 B2 | 3/2013 | Eide | |
| D679,379 S | 4/2013 | Katsura | |
| 8,444,592 B2 | 5/2013 | Williams | |
| 8,480,630 B2 | 7/2013 | Mudd | |
| D687,536 S | 8/2013 | Guarraia | |
| 8,545,440 B2 | 10/2013 | Patrick | |
| 8,562,600 B2 | 10/2013 | Kirkpatrick | |
| 8,684,947 B2 | 4/2014 | Eide | |
| 8,764,668 B2 | 7/2014 | Roteliuk | |
| 8,814,807 B2 | 8/2014 | Hulvershorn | |
| 8,896,324 B2 | 11/2014 | Kroh | |
| 8,926,525 B2 | 1/2015 | Hulvershorn | |
| 8,992,481 B2 | 3/2015 | Mudd | |
| 8,998,841 B2 | 4/2015 | Shen | |
| D730,514 S | 5/2015 | Boaz | |
| 9,044,542 B2 | 6/2015 | Patrick | |
| D734,475 S | 7/2015 | Ross | |
| D736,370 S | 8/2015 | Sabin | |
| D741,811 S | 10/2015 | Hochman | |
| 9,199,044 B2 | 12/2015 | Bangera | |
| 9,205,204 B2 | 12/2015 | Bangera | |
| 9,358,038 B2 | 6/2016 | Hulvershorn | |
| 9,358,350 B2 | 6/2016 | Bangera | |
| D760,888 S | 7/2016 | Friedrich | |
| D765,832 S | 9/2016 | Hochman | |
| 9,443,446 B2 | 9/2016 | Rios | |
| 9,452,261 B2 | 9/2016 | Alon | |
| 9,468,396 B2 | 10/2016 | Mahapatra | |
| 9,504,790 B1 | 11/2016 | Hochman | |
| 9,603,537 B2 | 3/2017 | Lechner | |
| 9,642,534 B2 | 5/2017 | Mahapatra | |
| 9,655,528 B2 | 5/2017 | Zhu | |
| D801,519 S | 10/2017 | Sabin | |
| D803,386 S | 11/2017 | Sabin | |
| D803,387 S | 11/2017 | Bodwell | |
| 9,888,881 B2 | 2/2018 | Hulvershorn | |
| 9,901,679 B2 | 2/2018 | Shen | |
| 9,956,341 B2 | 5/2018 | Hockman | |
| 10,004,450 B2 | 6/2018 | Moskowitz | |
| 10,117,673 B2 | 11/2018 | Luo | |
| 10,130,749 B2 * | 11/2018 | Schade | A61B 5/6866 |
| 10,220,180 B2 | 3/2019 | Hochman | |
| 10,383,610 B2 | 8/2019 | Moskowitz | |

(56) References Cited

U.S. PATENT DOCUMENTS

| | | | |
|---|---|---|---|
| D859,634 S | 9/2019 | Hochman | |
| 10,406,285 B2 | 9/2019 | Anand | |
| 10,463,838 B2 | 11/2019 | Hulvershorn | |
| 10,602,958 B2 | 3/2020 | Silverstein | |
| 2002/0016567 A1 | 2/2002 | Hochman | |
| 2002/0016569 A1 | 2/2002 | Critchlow | |
| 2002/0022807 A1 | 2/2002 | Duchon | |
| 2002/0143294 A1 | 10/2002 | Duchon | |
| 2003/0014006 A1 | 1/2003 | Alexandre | |
| 2004/0035743 A1 | 2/2004 | Tighe | |
| 2004/0149282 A1 | 8/2004 | Hickle | |
| 2004/0215080 A1 | 10/2004 | Lechner | |
| 2005/0004513 A1 | 1/2005 | Beyerlein | |
| 2005/0004514 A1 | 1/2005 | Hochman | |
| 2005/0096593 A1 | 5/2005 | Pope | |
| 2006/0122555 A1* | 6/2006 | Hochman | A61M 5/16854 |
| | | | 604/67 |
| 2006/0247657 A1 | 11/2006 | Trieu | |
| 2007/0038143 A1 | 2/2007 | Christensen | |
| 2007/0197922 A1 | 8/2007 | Bradley | |
| 2008/0058702 A1 | 3/2008 | Arndt | |
| 2008/0103408 A1 | 5/2008 | Denton | |
| 2008/0281265 A1 | 11/2008 | Hochman | |
| 2009/0131832 A1 | 5/2009 | Sacristan Rock | |
| 2009/0149911 A1 | 6/2009 | Dacey, Jr. | |
| 2009/0149912 A1 | 6/2009 | Dacey, Jr. | |
| 2009/0171191 A1 | 7/2009 | Patrick | |
| 2009/0210029 A1 | 8/2009 | Tsui | |
| 2009/0221914 A1 | 9/2009 | Barrett | |
| 2009/0326482 A1 | 12/2009 | Hochman | |
| 2010/0022918 A1 | 1/2010 | Fujie | |
| 2010/0030102 A1 | 2/2010 | Poston | |
| 2010/0049270 A1 | 2/2010 | Pastore | |
| 2010/0056932 A1 | 3/2010 | Roteliuk | |
| 2010/0179488 A1 | 7/2010 | Spiegel | |
| 2010/0274191 A1 | 10/2010 | Ting | |
| 2011/0021905 A1 | 1/2011 | Patrick | |
| 2011/0046477 A1 | 2/2011 | Hulvershorn | |
| 2011/0054353 A1 | 3/2011 | Hulvershorn | |
| 2011/0060229 A1 | 3/2011 | Hulvershorn | |
| 2011/0087166 A1 | 4/2011 | Davis | |
| 2011/0112511 A1 | 5/2011 | Singer | |
| 2011/0120566 A1 | 5/2011 | Ohmi | |
| 2011/0190596 A1 | 8/2011 | Hacker | |
| 2011/0270179 A1 | 11/2011 | Ouyang | |
| 2011/0288481 A1 | 11/2011 | Mudd | |
| 2011/0298628 A1 | 12/2011 | Vad | |
| 2011/0301500 A1 | 12/2011 | Maguire | |
| 2012/0022407 A1 | 1/2012 | Lechner | |
| 2012/0083760 A1 | 4/2012 | Ledford | |
| 2012/0101410 A1 | 4/2012 | Lechner | |
| 2012/0232389 A1 | 9/2012 | Guzman | |
| 2012/0259237 A1 | 10/2012 | Axelrod | |
| 2012/0289819 A1 | 11/2012 | Snow | |
| 2012/0296176 A1 | 11/2012 | Herbst | |
| 2013/0041258 A1 | 2/2013 | Patrick | |
| 2013/0053851 A1 | 2/2013 | Schmitz | |
| 2013/0131633 A1 | 5/2013 | Mudd | |
| 2013/0261533 A1 | 10/2013 | Norkunas | |
| 2014/0012226 A1 | 1/2014 | Hochman | |
| 2014/0066891 A1* | 3/2014 | Burns | A61M 5/484 |
| | | | 604/506 |
| 2014/0121636 A1 | 5/2014 | Boyden | |
| 2014/0121637 A1 | 5/2014 | Boyden | |
| 2014/0207050 A1 | 7/2014 | Gonzalez | |
| 2014/0221965 A1 | 8/2014 | Regittnig | |
| 2014/0316268 A1 | 10/2014 | Kafiluddi | |
| 2014/0343406 A1 | 11/2014 | Damjanovic | |
| 2015/0150519 A1 | 6/2015 | Glenn | |
| 2015/0283365 A1 | 10/2015 | Dacey, Jr. | |
| 2015/0374929 A1 | 12/2015 | Hyde | |
| 2016/0135712 A1 | 5/2016 | Holochwost | |
| 2016/0136363 A1 | 5/2016 | McClellan | |
| 2016/0228633 A1 | 8/2016 | Welsch | |
| 2017/0106142 A1 | 4/2017 | Hochman | |
| 2018/0064870 A1 | 3/2018 | Hochman | |
| 2018/0087517 A1 | 3/2018 | Glenn | |
| 2018/0116551 A1 | 5/2018 | Newman | |
| 2018/0228968 A1 | 8/2018 | Hochman | |

FOREIGN PATENT DOCUMENTS

| | | |
|---|---|---|
| EP | 0538259 | 4/1993 |
| FR | 2628625 | 9/1989 |
| HU | P8806113 | 10/1990 |
| HU | P0204296 | 3/2003 |
| JP | 5042218 | 2/1993 |
| JP | 6007440 | 1/1994 |
| JP | 6142114 | 5/1994 |
| WO | 1996005768 | 2/1996 |
| WO | 9725081 | 7/1997 |
| WO | 03000146 | 1/2003 |
| WO | 2010071416 | 6/2010 |
| WO | 2017066732 | 4/2017 |
| WO | 2018152225 | 8/2018 |
| WO | 2018204668 | 11/2018 |

OTHER PUBLICATIONS

Usubiaga et al., "Epidural Pressure and Its Relation to Spread of Anesthetic Solutions in Epidural Space", Anesthesia and Analgesia, vol. 46, No. 4, pp. 440-446, 1967.

Husemeyer et al., "Lumbar Extradural Injection Pressures N Pregnant Women", British Journal of Anaesthesia, 52, pp. 55-59, 1980.

Paul et al., "Extradural Pressure Following the Injection of Two Volumes of Bupivacaine", British Journal of Anaesthesia, 62, pp. 368-372, 1989.

Hirabayashi et al., "Effect of Extradural Compliance and Resistance on Spread of Extradural Analgesia", British Journal of Anaesthesia, 65, pp. 508-513, 1990.

Abstract of: Vas, "A study of epidural pressures in infants", Pediatric Anaesthesia, 11 (5), pp. 575-583, 2001.

Lechner et al., "Clinical results with a new acoustic device to identify the epidural space", Anesthesia, 57, pp. 768-772, 2002.

Gadsden et al., "Opening Injection Pressure Consistently Detects Needle-Nerve Contact during Ultrasound-guided Interscalene Brachial Plexus Block" Anesthesiology, vol. 120, No. 5, May 2014, pp. 1246-1253.

Cohen et al., "Functional deficits after intraneural injection during interscalene block", Regional Anesthesia and Pain Medicine, vol. 35, No. 4, Jul.-Aug. 2010, pp. 397-399.

Reiss et al., "Nerve injury complicating ultrasound/electrostimulation-guided supraclavicular brachial plexus block", Regional Anesthesia and Pain Medicine, vol. 35, No. 4, Jul.-Aug. 2010, pp. 400-401.

Lupu et al., "Nerve expansion seen on ultrasound predicts histologic but not functional nerve injury after intraneural injection in pigs", Regional Anesthesia and Pain Medicine, vol. 35, No. 2, Mar.-Apr. 2010, pp. 132-139.

Steinfeldt et al., "Histological consequences of needle-nerve contact following nerve stimulation in a pig model", Anesthesiology Research and Practice, vol. 2011, Feb. 2011, 9 pages.

Steinfeldt et al., "Forced needle advancement during needle-nerve contact in a porcine model: Histological outcome", Anesthesia & Analgesia, vol. 113, No. 2, Aug. 2011, pp. 417-420.

Sites et al., "Characterizing novice behavior associated with learning ultrasound-guided peripheral regional anesthesia", Regional Anesthesia and Pain Medicine, vol. 32, No. 2, Mar.-Apr. 2007, pp. 107-115.

Sites et al., "Incidence of local anesthetic systemic toxicity and postoperative neurologic symptoms associated with 12,668 ultrasound-guided nerve blocks", Regional Anesthesia and Pain Medicine, vol. 37, No. 5, Sep.-Oct. 2012, pp. 478-482.

Liu et al., "Incidence of unintentional intraneural injection and postoperative neurological complications with ultrasound-guided interscalene and supraclavicular nerve blocks", Anaesthesia vol. 66, 2011, pp. 168-174.

Abstract of: Bilbao et al., "Neurological complications associated with ultrasound-guided interscalene and supraclavicular block in

(56) References Cited

OTHER PUBLICATIONS elective surgery of the shoulder and arm. Prospective observational study in a university hospital", Rev Esp Anestesiol Reanim, vol. 60, No. 7, Aug.-Sep. 2013, pp. 384-391.

Widmer et al., "Incidence and severity of complications due to femoral nerve blocks performed for knee surgery", The Knee, Nov. 2012, 5 pages.

Hadzic et al., "Combination of intraneural injection and high injection pressure leads to fascicular injury and neurologic deficits in dogs", Regional Anesthesia and Pain Medicine, vol. 29 No. 5 Sep.-Oct. 2004, pp. 417-423.

Kapur et al., "Neurologic and histologic outcome after intraneural injections of lidocaine in canine sciatic nerves", ACTA, Anaesthesiologica Scandinavica, vol. 51, 2007, pp. 101-107.

International Preliminary Report on Patentability issued in International Patent Application No. PCT/US16/57264 dated Apr. 17, 2018.

"Medical Device Sanity"; http://mdgoo.blogspot.com/2014/12/another-medical-device-supplier-with.html; published prior to Oct. 27, 2017.

Al-Aamri, et al., "Reliability of Pressure Waveform Analysis to Determine Correct Epidural Needle Placement in Labouring Women", Anaesthesia 2017, 72, pp. 840-844.

Cohen et al, "Epidural Block for Obstetrics: Comparison of Bolus Injection of Local Anesthetic with Gravity Flow Technique", Journal of Clinical Anesthesia, 9, 1997, pp. 623-528.

Cohen et al, "Extradural Block in Obstetric Patients: Review of Experience with Gravity Administration", Acta Anaesthesiologica Scandinavica, 35, 1991, pp. 676-679.

Dawkins, "The identification of the epidural space" Anaesthesia, vol. 18, No. 1, Jan. 1963, pp. 66-77.

Examination Report issued in Australian Patent Application No. 2013287174 dated Oct. 26, 2016.

Extended European Search Report issued in EP Application No. 13813314.5 dated Feb. 18, 2016.

Gadsden, et al., "High Opening Injection Pressure Is Associated With Needle-Nerve and Needle-Fascia Contact During Femoral Nerve Block", Regional Anesthesia and Pain Medicine, vol. 41, No. 1, Jan.-Feb. 2016, pp. 50-55.

Ghelber et al., "Identification of the Epidural Space Using Pressure Measurement . . . ", Regional Anesthesia and Pain Medicine, vol. 33, No. 4, Jul.-Aug. 2008, pp. 346-352.

Ghia, et al, "Confirmation of Location of Epidural Catheters by Epidural Pressure Waveform and Computed Tomography Cathetergram", Regional Anesthesia and Pain Medicine, vol. 26, No. 4 (Jul.-Aug.), 2001, pp. 337-341.

Gong et al, "Pressure Waveform-Guided Epidural Catheter Placement in Comparison to the Loss-of-Resistance Conventional Method", Journal of Clinical Anesthesia, 26 (2014) pp. 395-401.

Hettiarachchi et al, "The Effect of Pulsatile Flow on Intrathecal Drug Delivery in the Spinal Canal", Annals of Biomedical Engineering, vol. 39, No. 10, Oct. 2011, pp. 2592-2602.

Hilber et al, "A systematic review of the diagnostic accuracy of epidural wave form analysis to identify the epidural space in surgical and labor patients", http://www.minervamedica.it, Minerva Anestesiologica, Apr. 2019, 85(4), pp. 393-400.

Hong et al, "Analysis of Epidural Waveform for Cervical Epidural Steroid Injections Confirmed with Fluoroscopy", An.md-journal.com, Hong and Jung Medicine (2018) 97:13, 4 pages.

Hsu et al, "The Frequency and Magnitude of Cerebrospinal Fluid Pulsations Influence Intrathecal Drug Distribution: Key Factors for Interpatient Variability", www.anesthesia-analgesia.org, vol. 115, No. 2, Aug. 2012, pp. 386-394.

http://www.anteis.com/AestheticDermatology/injectionsystem.php, published prior to Feb. 15, 2017.

http://www.intranixtech.com/myoguide-system/, published prior to Feb. 15, 2017.

https://www.dermaqueen.co.ki7, published prior to Feb. 15, 2017.

Hungarian Novelty Report for Application No. P 04 00176.

Iff et al., "The Use of an Acoustic Device to Identify the Epidural Space in Cattle", The Veterinary Journal, 187 (2011) pp. 267-268.

Iff et al., "The Use of an Acoustic Device to Identify the Extradural Space in Standing Horses", Veterinary Anesthesia and Analgesia, 37 (2010) pp. 57-62.

Iff, Isabelle, et al., "The use of an acoustic device to identify the extradural space in standing horses", Veterinary Anaesthesia and Analgesia, 2010, 37, 57-62.

International Preliminary Report on Patentability for PCT/US2013/045142 filed on Jun. 11, 2013.

International Preliminary Report on Patentability issued in International Application No. PCT/US06/29091 dated Feb. 28, 2008.

International Preliminary Report on Patentability issued in International Application No. PCT/US13/45142 dated Jan. 15, 2015.

International Search Report & Written Opinion issued in International Application No. PCT/US13/45142 dated Sep. 10, 2013.

International Search Report and Written Opinion issued in International Application No. PCT/US18/31096 dated Sep. 10, 2018.

International Search Report and Written Opinion issued in PCT/US16/63861 dated Mar. 6, 2017.

Jonathan Dillon, "Embedded storage in disposable medical items"; Article posted on Aug. 1, 2011; https://www.electronicproducts.com/Digital_ICs/Memory/Embedded_storage_in_disposable_medical_items.aspx.

Lechner et al., "Clinical Results with the Acoustic Puncture Assist Device, a New Acoustic Device to Identify the Epidural Space", Anesthesia Analgesia, (2003) pp. 1183-1187.

Lechner et al., "Thoracic Epidural Puncture Guided by an Acoustic Signal: Clinical Results", European Journal of Anesthesiology, 21 (2004) pp. 694-699.

Lechner, T.J.M. et al., "The use of a sound-enabled device to measure pressure during insertion of an epidural catheter in women in labour", Anaesthesia, 2011, 66, pp. 568-573.

Lennox et al, "A Pulsatile Pressure Waveform Is a Sensitive Marker for Confirming the Location of the Thoracic Epidural Space", Journal of Cardiothoracic and Vascular Anesthesia, vol. 20, No. 5 Oct. 2006, pp. 659-663.

Leurcharusmee et al, "Reliability of Waveform Analysis as an Adjunct to Loss of Resistance for Thoracic Epidural Blocks", Regional Anesthesia and Pain Medicine, vol. 40, No. 6, Nov.-Dec. 2015, pp. 694-697.

Maxim Integrated Product Specification for DS28EC20 20Kb 1-Wire EEPROM; published prior to Oct. 27, 2017.

McKendry et al., "Pressure Waveforms to Assess Epidural Placement: Is There a Role on Delivery Suite?", Anaesthesia, 72, 2017, pp. 815-820.

NL Search Report, NL 2002708, dated Oct. 9, 2009.

Official Action issued in U.S. Appl. No. 11/208,400 dated May 29, 200810 pages.

PCT International Prelminary Report on Patentability, PCT/NL2010/000061, dated Oct. 4, 2011.

PCT International Search Report, PCT/NL2010/000061, dated Aug. 23, 2010.

Product brochure "PAJUNK: NerveGuard Automatic system for injection pressure limitation" (XS200192B) dated Jan. 2017, 4 pages.

Ross et al., "Pressures of Injection in a Cadaver Model of Peripheral Nerve Blockade", Journal of Anesthesia & Clinical Research, 2014, vol. 5, Issue 10, 4 pages.

Suwa et al, "Pressure-Guided Method for Identification of the Epidural Space in Children", Anesthesiology, vol. 89, No. 2, Aug. 1998, pp. 546-548.

Tsui et al., "Reduced Injection Pressures Using a Compressed Air Injection . . . ", Regional Anesthesia and Pain Medicine, vol. 33, No. 2, Mar.-Apr. 2008, pp. 168-173.

Wagshul et al, "The pulsating brain: A review of experimental and clinical studies of intracranial pulsatility", http://www.fluidsbarrierscns.com/content/8/1/5, 2011, 8:5, 23 pages.

Lacoste, "DSSS in a nutshell the Powerof Patterns at Play", Circuit Cellar, Apr. 2020, #357, pp. 62-67.

(56) References Cited

OTHER PUBLICATIONS

International Search Report & Written Opinion issued in International Application No. PCT/US20/29857 dated Jul. 21, 2020.

* cited by examiner

DEVICE AND METHOD FOR IDENTIFICATION OF A TARGET REGION

RELATED APPLICATIONS

This application is a continuation of U.S. application Ser. No. 17/096,411, filed Nov. 12, 2020, which is a continuation of International Application No. PCT/US20/22910, filed Mar. 16, 2020, which claims the benefit of priority of U.S. application Ser. No. 16/414,499, filed on May 16, 2019, now U.S. Pat. No. 10,646,660 issued May 12, 2020, the entire contents of which application(s) are incorporated herein by reference.

TECHNICAL FIELD

The present invention relates generally to methods and apparatus for use in locating a target region which is situated in a body of a subject, for example for the delivery of drugs.

BACKGROUND

Locating a target region in a body, for example an anatomical cavity in a body of a patient, is important, inter alia, for anesthetics, or biopsy or aspiration of material from the cavity.

For example, a regional anesthesia block of the epidural tissue-space is understood to produce effective transient anesthesia of the lower extremities of the body. It can be effectively used for a vast number of invasive procedures of the body, including but not limited to, childbirth, prosthetic hip replacement, and a variety of other surgical procedures where anesthesia below the waist is required. It can also be effectively used for treatment of chronic and acute pain including, for example, "back-pain," ailments of the vertebrae and, compression of the accessory nerves of the spinal column. To achieve effective regional anesthesia and to block nerve transmission to the central nervous system an adequate volume of a local anesthetic solution must be deposited in close proximity to the spinal cord at a particular level of the vertebral column within the anatomic site known as the epidural space.

The epidural space is that part of the vertebral canal not occupied by the dura mater and its contents. It lies between the dura and the periosteum lining the inside of the vertebral canal. It extends from the foramen magnum to the sacral hiatus. The anterior and posterior nerve roots in the dural membrane pass across the epidural space to unite in the intervertebral bodies, and the intravertebral discs. Laterally, the epidural space is bordered by the periosteum of the vertebral pedicles, and the intervertebral foramina. Posteriorly, the bordering structures are the periosteum of the anterior surface of the laminae, the articular processes and their connecting ligaments, the periosteum of the root of the spines, and the interlaminar spaces filled by the ligamentum flavum. The space contains venous plexuses and fatty tissue which is continuous with the fat in the paravertebral space.

The epidural fluid filled space (posterior epidural space) is a limited anatomic area with an irregular shape measuring in several square millimeters with respect to the cross section of the vertebrae and spinal column. The fluid filled space is very narrow and is associated closely with the dura of the spinal column with the ligamentum flavum closely adjacent. The fluid filled space therefore has to be clearly identified when the bevel or point of the needle exits the ligamentum flavum, as the dura will be punctured if the needle continues to penetrate. The standard technique for locating the epidural fluid filled space employs the loss-of-resistance (LOR) technique. This technique utilizes a low-friction syringe made of plastic or glass connected to an epidural Touhy needle (16 to 18 gauge). In addition, other pump driven systems have been developed to identify the epidural space by utilizing pressure monitoring with visual and acoustical representation of the fluid pressure within the system or at the tip of the needle.

When using a LOR technique the needle of the syringe is advanced until the subjective "feel" of resistance by the clinician results in a distinct back-pressure on the plunger. The clinician must subjectively differentiate the back-pressure or resistance encountered to identify the location of the anatomic structure of the ligamentum flavum. The epidural fluid filled space is entered by the tip of the needle after it passes through the ligamentum flavum thus identifying a true-LOR.

During the advancement of the needle within the tissues it is common for the operator to identify a drop of pressure, or a false-LOR. The false-LOR can be attributed to the needle tip entering into a low-density tissue structure such as a vacuole (adipose tissue) or an anatomic structure with a high tissue compliance such as the interspinous tissues. Repositioning of the needle (forward and backward) occurs many times as a needle makes contact to bony vertebrae as one is attempting to find the correct trajectory to the epidural space. Any backward movement (retraction) of the needle along a path during the repositioning creates a drop in pressure in the fluid, which can result in a false-LOR further complicating the detection of a true-LOR.

Various conditions can create a false-LOR. False-LORs can lead to many problems. For example, excess fluids can be indiscriminately injected while trying to determine the location of the epidural space. The additional fluid released into these tissues can further complicate the identification of epidural space. Additionally, if the doctor has difficulty discriminating between a false-LOR and a true-LOR, the Touhy needle may be moved beyond the boundary of the epidural space and inadvertently advanced into and through the dura of the spinal cord producing what is termed a wet-tap, which can have dangerous long-term consequences to the patient.

Therefore, it is desirable to provide a system that supplements or supplants the loss of resistance information to accurately guide a needle during insertion.

SUMMARY OF THE INVENTION

The present invention provides a method and apparatus or device that enables practitioners to more easily perform the identification of anatomical target regions such as the epidural space.

The present invention provides a novel system for guiding a needle to an anatomical target region. The system provides a software logic and apparatus that can simplify discrimination between a false-LOR and true-LOR when performing these operations, such as detection of the epidural space, thereby improving the reliability and safety of such injections.

According to a first aspect, the present invention provides a needle bearing apparatus for administering fluid into an anatomic space of a mammalian subject. The apparatus includes a fluid reservoir for storing fluid to be provided to the needle, an ejection element displaceable relative to the fluid reservoir to expel fluid from the reservoir and a drive element configured to engage the ejection element to control displacement of the ejection element. A controller is provided for controlling the drive element to control the flow of fluid from the reservoir to the needle. Additionally, the apparatus includes a sensor for detecting a characteristic indicative of the fluid pressure in the needle. The sensor is configured to continuously detect the characteristic as the needle-bearing apparatus is inserted into the subject. A flexible conduit is in fluid communication with the fluid reservoir and the sensor; and the conduit is substantially rigid radially. The controller periodically discontinues movement of the drive element and processes data from the sensor to detect one or more characteristics indicative of a pulsatile waveform. Additionally, the conduit, reservoir, ejection element and drive element are configured so that the fluid volume between the needle and the fluid reservoir is substantially constant so that the sensor is able to accurately detect the pulsatile waveform passing through residual fluid in the needle when movement of the drive element is discontinued. Optionally, the fluid reservoir may be a syringe barrel. Additionally, the ejection element may be slidably displaceable within the fluid reservoir.

According to a further aspect, the invention relates to a controller configured to analyze the data from the sensor to detect one or more characteristics indicative of a loss of resistance.

According to yet another aspect the invention provides a system in which in response to detecting one or more characteristics, the controller discontinues movement of the drive element and processes data from the sensor to detect one or more characteristics indicative of a pulsatile waveform. Optionally, the controller may be configured to provide a verification signal that the needle is properly placed adjacent a target tissue upon receipt of a signal indicative of a loss of resistance and upon receipt of a signal indicative of the presence of a pulsatile waveform at the needle.

Yet another aspect of the invention provides a display including a first output section configured to display the fluid pressure at the needle as a function of time in a manner consistent with a loss of resistance guidance procedure. Additionally, the controller may be configured to process data from the sensor to isolate data indicative of a pulsatile waveform. The display may comprise a second output section configured to display the data indicative of a pulsatile waveform while the first section displays the fluid pressure data as a function of time in the first section.

The present invention also provides a method for locating a target region which is situated in a body of a subject with a needle in fluid communication with a reservoir. The method includes the steps of providing a reservoir containing injection fluid, tubing in communication at one end with the reservoir and connected at the other end to the needle to be inserted into the body of the subject and the step of acquiring data about a resistance measurement of the injection fluid when the fluid is pumped into the body of the subject through the needle. The method further includes the steps of advancing the needle into the patient. Additionally, the method may include the step of pumping injection fluid into the patient during the step of advancing the needle. Still further, the method may include the step of intermittently discontinuing the step of advancing the needle and the step of pumping injection fluid. The method may also include the step of acquiring data regarding the fluid pressure in the needle during the step of intermittently discontinuing and processing the data acquired during the step of intermittently discontinuing to detect one or more characteristics indicative of a pulsatile waveform at the needle.

Optionally, another aspect of the invention comprises re-starting the steps of advancing the needle and pumping injection fluid after the step of intermittently discontinuing.

Additionally, another aspect includes the step of processing the data regarding fluid pressure in the needle by removing noise related to the flow of fluid when the fluid is pumped into the body. The pump may be operable to pump fluid during the step of pumping injection fluid and the step of removing noise may include the steps of running the pump prior to inserting the needle into the body of the subject and acquiring data related to noise during the step of running the pump. Further still, the step of removing noise may comprise modifying the data regarding fluid pressure in response to the data acquired related to noise.

According to another aspect, the invention provides a method including the step of selectively varying an amplitude range for processed fluid pressure data to attempt to identify a pulsatile waveform.

A still further aspect of the invention provides a method for inserting a needle into a patient. The method includes the step of performing a loss of resistance procedure to attempt to place a needle at a target location in the patient, wherein the step of performing a loss of resistance procedure comprises the steps of: inserting the needle into the patient, injecting fluid through the needle during the step of inserting, detecting the fluid pressure at the needle during the step of injecting, and guiding the needle in response to the step of detecting the fluid pressure. The presence of a pulsatile waveform at the needle is detected, which may include the steps of detecting the fluid pressure at the needle when the needle is substantially stationary in the patient and injecting a bolus of medication into the patient after the step of performing a loss of resistance procedure indicates that the needle is at the target location and after the step of detecting the presence of a pulsatile wave indicates the presence of a pulsatile waveform.

Optionally, the method may include the step of intermittently switching between the step of performing a loss of resistance procedure and the step of detecting the presence of a pulsatile waveform. Additionally, the step of injecting fluid comprises electronically controlling a drive unit to dispense fluid from a fluid reservoir. Further, the step of injecting comprises electronically controlling the drive unit in response to the step of detecting the fluid pressure.

Yet another aspect of the present invention is an apparatus for locating a target region which is an anatomic space situated in a body of a subject. The apparatus includes a reservoir for receiving an injection fluid, a needle in fluid communication with the reservoir, and a sensor operable to detect a characteristic indicative of the fluid pressure in the needle. A pump is configured to pump fluid to the needle from the reservoir and a controller is operable to process data from the sensor regarding the fluid pressure in the needle. The controller is configured to process the data from the sensor when the needle is stationary to identify a pulsatile waveform. Additionally, the controller is configured to provide signals to guide insertion of the needle wherein the signals are provided in response to the data from the sensor. Further, wherein the system comprises an input mechanism for selectively varying an amplitude range for the processed data to identify a pulsatile waveform.

These and other embodiments are described in more detail hereinafter. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which a preferred embodiment of the invention is illustrated.

DETAILED DESCRIPTION OF THE PREFERRED EMBODIMENTS

While the methods and apparatus are described herein by way of example for several embodiments and illustrative drawings, those skilled in the art will recognize that the inventive methods and apparatus for sorting items using a dynamically reconfigurable sorting array are not limited to the embodiments or drawings described. It should be understood, that the drawings and detailed description thereto are not intended to limit embodiments to the particular form disclosed. Rather, the intention is to cover all modifications, equivalents and alternatives falling within the spirit and scope of the methods and apparatus for detecting a pulsatile waveform and using the detection of a pulsatile waveform to guide or verify placement of a needle or other conduit. Any headings used herein are for organizational purposes only and are not meant to limit the scope of the description or the claims. As used herein, the word "may" is used in a permissive sense (i.e., meaning having the potential to), rather than the mandatory sense (i.e., meaning must). Similarly, the words "include", "including", and "includes" mean including, but not limited to.

Figure 1:
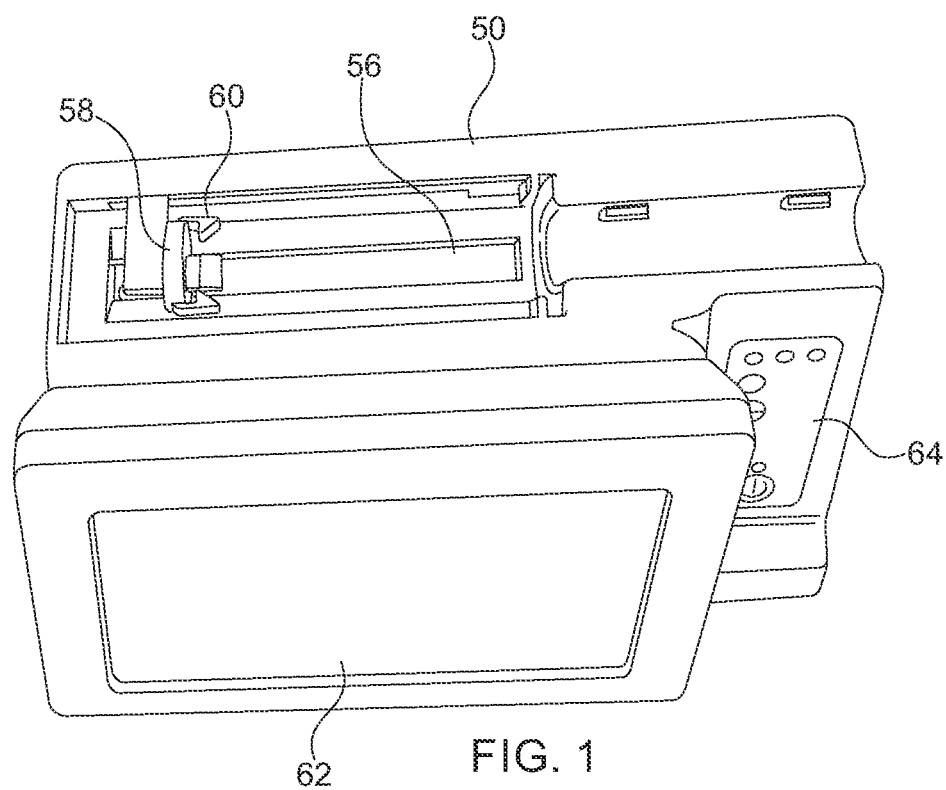
FIG. 1 is a top view of a computer-controlled drug delivery system.
Figure 2:
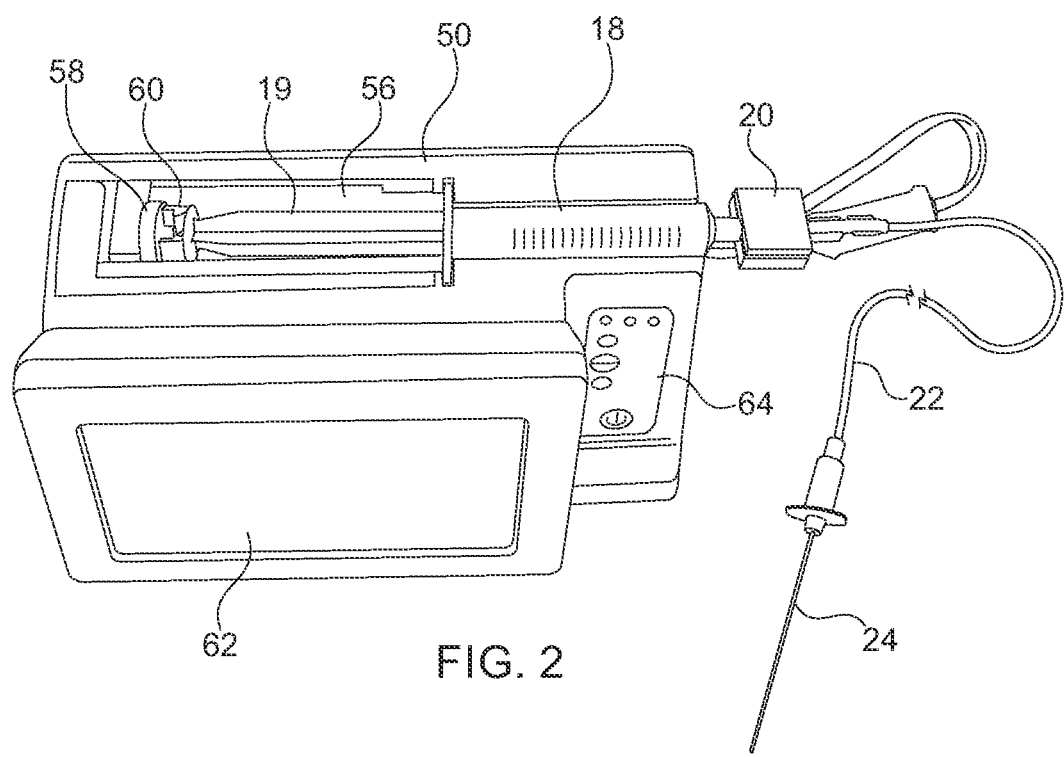
FIG. 2 is a top view of the drug delivery system illustrated in FIG. 1 with a disposable injection assembly connected with the system.
Figure 3:
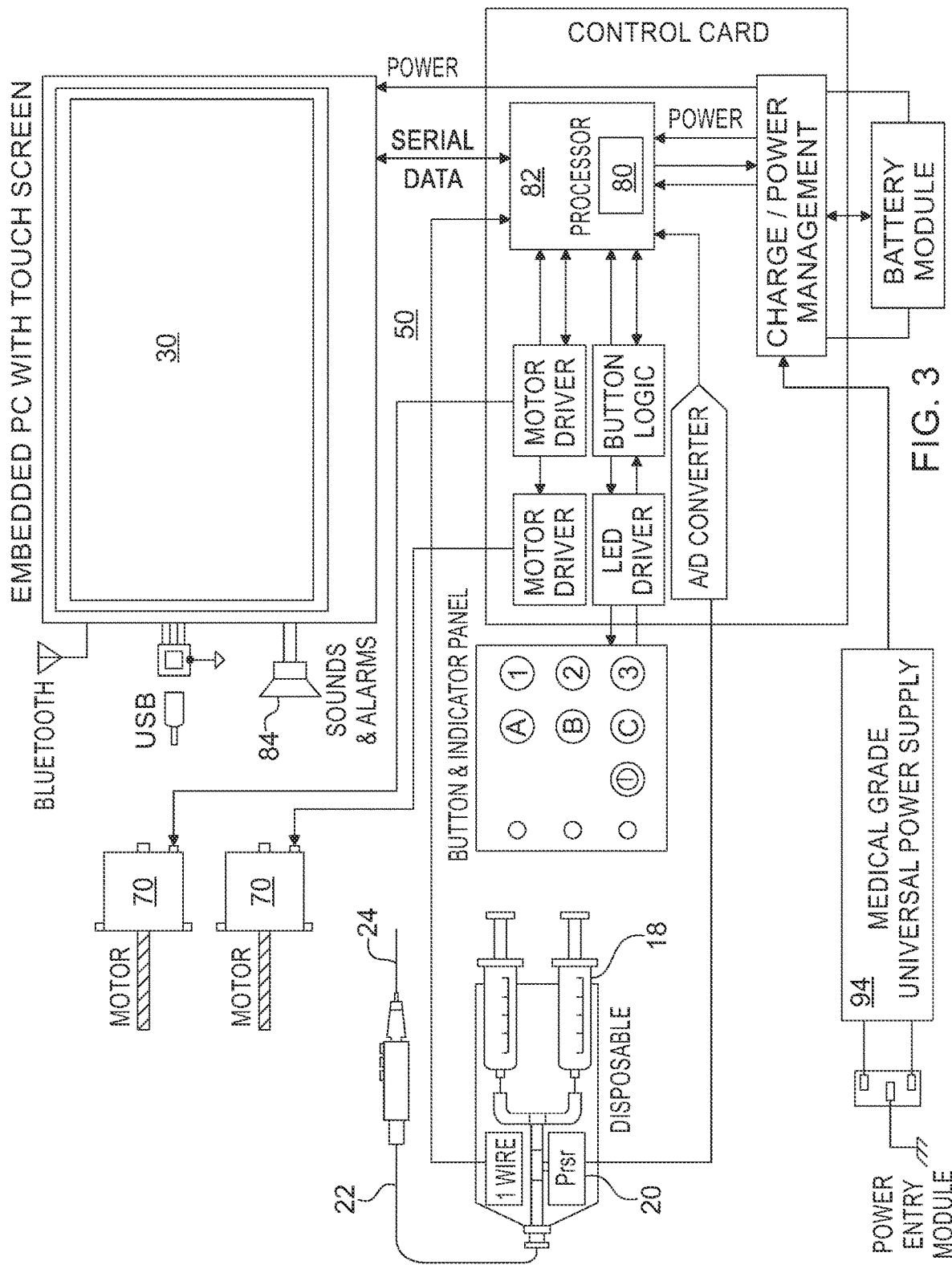
FIG. 3 is a schematic representation of the computer-controlled drug delivery system illustrated in FIG. 1.

Referring now to the drawings, in general and to FIGS. 1-3 specifically, a drug infusion system is designated generally 10. The system 10 includes an injection assembly 20 and a computer-controlled drug delivery instrument 50, referred to as a drive unit. The injection assembly 20 includes an insertion needle 24 configured for insertion into a mammalian subject. The injection assembly 20 is connected with the drive unit 50, which controls the flow of fluid to the injection assembly during use. The system 10 also includes one or more output mechanisms that provide data to the medical professional during a procedure to assist in proper placement of the needle in the subject.

The system 10 enables a practitioner to accurately identify a target tissue. In particular, the system may be adapted for use in identifying the location for injection of a drug while limiting the placement of drugs into non-targeted tissues. This may be performed for both diagnostic and therapeutic procedures. The system 10 utilizes the pressure of a fluid as it flows from a needle or catheter following placement of the needle/catheter within the tissue in order to identify the accuracy of placement and to monitor the placement during an injection or aspiration. System 10 may utilize a continuous flow of fluid at what is considered a slow flow-rate. In the present instance, a slow flow-rate is defined as a constant flow-rate between 0.01 mL/sec to 0.20 mL/sec. The continuous flow of fluid maintains a constant column of fluid that may enable a virtually instantaneous reaction time to pressure changes within the tissues to be detected. Generally, a flow-rate of between 0.005 cc/sec to 0.20 cc/sec will be appropriate for the subject and intervention, though 0.01 to 0.15 cc/sec may be preferred.

As discussed further below, the system is adapted for identifying proper placement of a needle according to various criteria. For instance, the system may identify a space such as the epidural space using a loss of resistance technique. Additionally, the system 10 may be adapted for identifying target tissue based on identifying a pulsatile waveform. In this way, the system may identify proper placement of the needle relative to a target tissue using a first search criteria and the system may verify or validate the proper placement of the needle relative to the target tissue using a second search criteria, such as the identification of a pulsatile waveform.

The flow-rate range provided by the drive unit 50 during the placement of the needle is capable of providing a responsiveness to a change in pressure that can be detected rapidly. Additionally, the system 10 includes one or more output mechanisms for providing audible and/or visual feedback of the detected fluid pressure in the insertion needle. The operator uses the feedback as guidance during the placement of the insertion needle. As shown in FIG. 2, the first output mechanism may be a video display screen, such as an LCD display for displaying data to aid the operator. Additionally, a second output mechanism may also be provided. For example, the second output mechanism may be a speaker 84 for providing an output signal.

Injection Assembly

Referring to FIG. 2, the system 10 includes an injection assembly 20 co-operable with a drive unit 50 during a drug infusion procedure. The injection assembly includes a syringe 18, a handpiece or needle 24 and a fluid line 22 connecting the syringe with the handpiece.

Various elements of the injection assembly may be disposable, such as the syringe 18, the fluid line 22, and/or the needle 24. Alternatively, the elements may be re-useable. Accordingly, various elements of the injection assembly may be releasably connectable. For instance, the fluid line 22 may include a fluid connector at each end. The fluid-tight connectors may be any of a variety of connectors. One such connector is a Luer connector. At the first end, the fluid connector sealingly connects with the syringe and at the second end the fluid line sealingly connects with the needle 24. Alternatively, the fluid line 22 may be fixedly connected with the rearward end of the needle 24. In either embodiment, the needle 24 and the syringe are in fluid communication to provide a flow of fluid from the syringe to the needle.

The syringe 18 may be any of a variety of hypodermic syringes and the size may vary depending on the intended use. The syringe 18 includes a barrel for holding a volume of medicament and a plunger 19 slidable within the barrel to draw fluid into or eject fluid from the barrel. The syringe 18 preferably also includes flanges projecting outwardly from the barrel. The flanges operate as finger flanges to facilitate displacement of the plunger into the barrel.

The injection assembly 20 also includes a pressure sensor 20 for detecting fluid pressure in the injection assembly. The pressure sensor may be disposed in one of several locations to measure a pressure that correlates with the fluid pressure at the tip of the needle 24. Alternatively, rather than or in addition to an in-line pressure sensor, the pressure sensor may be a force sensor located within or connected to the thumb plate that drives the syringe plunger 58 or a force sensor that is internal to the drive unit 50 that measures the force applied to the syringe plunger. Such a force sensor detects the force required to inject the fluid, which is related to the fluid pressure the fluid pressure in the needle. Using such a sensor, the detected force is converted to a pressure value by a calculation via the processor. In the present instance, the pressure sensor 20 is an inline fluid pressure sensor attached to the syringe 18 between the syringe and the tubing 22. In this way, the pressure sensor 20 senses the fluid pressure as the fluid exits the syringe and enters the tubing 22 to which the insertion needle 24 is connected. Similarly, the in-line pressure sensor can be interposed between the tubing and the needle. As shown in FIG. 2, the insertion needle 24 is connected to the forward end of the handpiece and the tubing 22 is connected to the rearward end of the handpiece.

The tubing 22 comprises an elongated polymer tube that is sufficiently flexible longitudinally to allow the tube to bend during use, but substantially non-expanding radially with a rigid wall thickness. In particular, the tube is a polymer tubing that remains rigid radial without any radial at pressures below 500 mm/Hg The injection assembly 20 may be manually operated to inject fluid. However, in the present instance, a computer-controlled drug delivery system 50 controls the flow of fluid from the injection assembly as discussed further below. An electrical cable connects the pressure sensor 20 with the drug delivery system 50 so that the drug delivery system can monitor and, if desired, vary the flow of fluid from the syringe in response to the data from the pressure sensor 20. The pressure transducer 20 may be connected inline between the forward end of the cylinder of syringe 18, and the first end of tubing 22. One such connection is a Luer connection for connecting the pressure transducer 20 to the tip of the syringe, although other connections may be used. The connection may be fixed by a threaded connection and/or an irreversible threaded connection, such as a Luer-Lock. Alternatively, the pressure transducer 20 may be permanently fixed to the syringe by plastic welding or chemical binding, such as adhesive. In this way, the instantaneous, actual fluid pressure in the drug delivery line 22 is sensed and used by the instrument, thereby providing a close approximation to the actual, instantaneous fluid pressure at the point or tip of the needle 24, and therefore, at the location in the patient's body where the needle tip is located. The electronic pressure transducer 20 provides pressure data via an electronic data cable that is connected directly to the central unit 50 to collect the pressure measurements.

The electronic pressure transducer 20 can be any of various pressure sensors. One type of sensor is a piezoelectric pressure sensor, such as sensors available from Merit Medical Systems, Inc. such as the Meritrans® Pressure Transducer item MER212.

Automated Fluid Delivery System

As described above, the system 10 may include a fluid delivery system 50 for providing a controlled flow of medication to the injection assembly 20. Preferably the fluid delivery system is an automated system and in the present instance is a computer-controlled fluid delivery system referred to as a drive unit 50.

Referring to FIGS. 1-3, the drive unit 50 is designed to work in connection with an injection element, such as syringe 18. The drive unit 50 may include a cradle 56 configured to receive the syringe 18 and a clamp for retaining the syringe in the cradle. The drive unit 50 includes a drive element 58 operable to drive the plunger in the syringe to expel fluid from the syringe. The drive unit 50 controls the displacement of the drive element 58 thereby controlling ejection of fluid from the syringe. In the present instance, the drive element may include a motor 70 driving an arm 58 having a clamp with a plurality of fingers 60 that releasably engage the plunger 19. The cradle 56 includes a recess for receiving the syringe is configured to constrain the syringe against longitudinal movement. For instance, the cradle 56 may include a slot for receiving the flange the projects radially outwardly from the surface of the syringe barrel. Accordingly, driving the motor in a first direction drives the arm 58 forwardly to advance the plunger 19. Since the barrel of the syringe is maintained in a relatively fixed axial position, displacement of the plunger displaces the plunger relative to the barrel, thereby expelling fluid. The CPU 82 of the drive unit provides signals to the motor to control operation of the motor.

The drive unit 50 is operable to provide constant or variable fluid flow. In the present instance, the drive unit may provide a continuous fluid in response to signals received from the electronic pressure transducer 20, which continuously senses the pressure of the fluid during an insertion/injection procedure. Based on a pre-determined pressure, the drive unit 50 may stop the flow of fluid when the detected pressure exceeds a pre-defined threshold. The pre-defined threshold may be set by the practitioner and stored in a memory 80 of a microprocessor or computer 82 of the electronics in drive unit 50. Similarly, based on a pre-determined pressure, fluid-flow will resume when the fluid pressure falls below a pre-determined pressure and will continue to flow while the pressure remains below the threshold. The same pre-determined pressure may be used to control the stopping and re-starting of the fluid flow. In such case, as fluid initially enters the tissue the pressure will build to a pre-determined level and then stop until once again the pressure drops below this pre-determined level. Once the fluid pressure falls below the pre-determined level, the fluid-flow will resume and be maintained on a continuous basis. In this way, the flow of fluid may start and stop during the procedure creating an interruption of fluid flow once a specific pre-determined pressure is detected The system may include pre-defined pressure thresholds used to control the flow of medication from the syringe 18 during the procedure. This enables a clinician to selectively inject drugs into specific sites and intended tissues for diagnostic and therapeutic procedures. Pre-selected maximum allowable pressure limits and/or flow rates are stored in memory 80 and define either the maximum recommended pressures, or other criteria. As the pressure approaches this limit, a visual and/or audible alarm is generated for the clinician, i.e. on screen 62 and via speaker 84 that is activated by data from the microprocessor 82. In addition, data descriptive of the whole injection process is stored for future analysis in memory 80.

The system 10 may directly measure the fluid pressure in the injection assembly 20 or the system may measure a characteristic indicative of the fluid pressure in the injection assembly. For instance, the pressure may be measured by detecting the pressure resistance measured during infusion. The pressure resistance measured is converted into a visual signal on a continuous basis during the insertion procedure. The flow rate of medication during the procedure may be based on the fluid pressure detected in real time during the procedure. Therefore, the flow rate of the medication may be variable and may be dependent on the pressure in the system. In this way, the fluid pressure may be the primary controlling variable of the system.

One feature of the present system is the ability to detect minute changes in pressure at the needle tip while a needle is placed within the patient's tissue. One characteristic that facilitates the detection of minute pressure changes is the constant movement of fluid into the tissues under controlled conditions thus enabling one to identify and or avoid undesirable locations based on pressure within the tissue. The system detects these minute changes in pressure in real-time and dynamically when a continuous flow of the fluid is used. This continuous flow may be coordinated with a pre-determined maximum pressure used by the system to stop the flow of fluid at a pre-determined pressure limit to avoid damage to these tissues. With a constant flow of fluid, the head pressure provides the needed resistance within the tissues to enable subtle changes in the tissue density and compliance to be detected on a virtually instantaneous basis.

Another aspect that facilitates the detection of minute changes in pressure is the precise control of the volume of the injections set 18. Specifically, the tubing 22 of the injection assembly 20 is substantially rigid radially so that the tubing does not expand radially under pressures below 500 mmHg. Therefore, under any backpressure that the injection assembly 20 could reasonably expect during use the tubing will not expand or bulge so that the volume of the tubing will not expand from any back pressure that the injection assembly may encounter. Additionally, the drive unit 50 rigidly controls the position of the plunger relative to the syringe barrel to precisely control the volume inside of the barrel. Specifically, the drive unit controls the position of the plunger so that when the motor of the drive unit stops the drive unit maintains the plunger in a fixed position against forward or rearward displacement. In this way, the drive unit impedes or prevents movement of the plunger in response to fluid backpressure. Under normal operating conditions of the system, the drive unit maintains the plunger in a fixed position against any back pressure that the system may reasonably encounter during use. In this way, when the motor of the drive unit stops, the drive unit acts as a stop preventing relative displacement of the plunger relative to the barrel. These mechanical elements combined with the rigidity of the materials used in assembly 20 prevent deformation at pressures below 500 mmHg, which could impede detection of subtle pressure changes within the fluid being detected by sensor 20. In particular, when the drive unit is stopped, the configuration of the injection assembly 20 and the drive unit impede a change in fluid volume that affect detection of the pulsatile wave form.

The flow-rate, therefore, becomes another variable that may be modulated within a pre-determined range to maintain the desired fluid flow. In one specific embodiment, the fluid flow is stopped when the pressure exceeds a pre-determined threshold (maximum pressure). The flow-rate, as a second variable, may be limited so that fluid injections are not unduly rapid under low pressure conditions. It is contemplated that the relationship between pressure and fluid flow rate may either be binary or continuous. A binary relationship exists when the injection device is configured to deliver fluid at a single, pre-determined flow-rate for any pressure less than the pre-set maximum. Thus, the fluid flow is either on or off based on whether or not the pressure exceeds the threshold. Alternatively, the flow-rate may be modulated as a function of pressure. In this case, flow-rate will be reduced as the maximum pressure is approached and increased as the pressure drops. Optionally, the flow-rate may be limited to a first pre-set maximum pressure and a flow rate resumes at a second distinct pre-determined pressure.

As mentioned above, the system 10 may include a mechanism for displaying relevant injection data including, for example, instantaneous flow-rates, pressures, and injection amounts upon a screen 30 of the drive unit 50. Similarly, the system may include a mechanism for recording such information for subsequent analysis after the procedure is performed. For instance, the system may include a non-volatile electronic storage medium, such as a hard drive, flash drive, optical drive or other medium for storing electronic data.

All measurements and information may be presented to the clinician in "real-time" so that the clinician may determine whether the injection is being delivered to the intended location and/or correct tissues and may modify the injection technique accordingly. In addition, the measurements may be recorded for later review and documentation of the clinical event.

It is also contemplated that multiple syringes driven by separate syringe plungers may be used to allow multiple drugs to be injected as well as a second syringe drive that does not required a pre-determined pressure to be reached for any said purpose. The second drive can be programmed on a specific flow-rate to allow infusion of a drug such as local anesthetic and other therapeutic drugs into a variety of tissues.

In yet another embodiment the device may contain two distinct syringe drives in which both are capable of modulation based on fluid-pressure as previously herein described.

Calculation of Fluid Pressure at the Exit of the Needle

As discussed above, the fluid pressure may be used to control operation of the system 10. For instance, the system may provide a signal to the operator when the fluid pressure exceeds a threshold, thereby indicating that the needle may be located against or in dense tissue, such as the dura. There are several methodologies for calculating the fluid pressure at the exit of the needle.

A pressure sensor may detect the fluid pressure in the injection assembly 20. For example, as discussed above the pressure sensor may be an in-line pressure sensor. Alternatively, a pressure sensor internal to the drive unit 50 may detect the fluid pressure between a conduit, such as tubing 22 and a fluid reservoir, such as a syringe 18, fluid-filled carpule or other fluid reservoir. Similarly, the pressure sensor can be interposed between the syringe tubing 22 and the needle 24. Further still, the in-line sensor may be embedded into a hub connected to the needle or between the tubing 22 and the hub. Another alternative is using a thumb-pad force sensor to detect the force driving the plunger 19 to calculate the pressure within the syringe 18. A command signal from the pressure sensor sends data of pressure to the CPU for calculation to determine the exit-pressure. The exit-pressure value is used to control the motor 70 that controls the flow of fluid from the syringe 18.

Figure 4A:
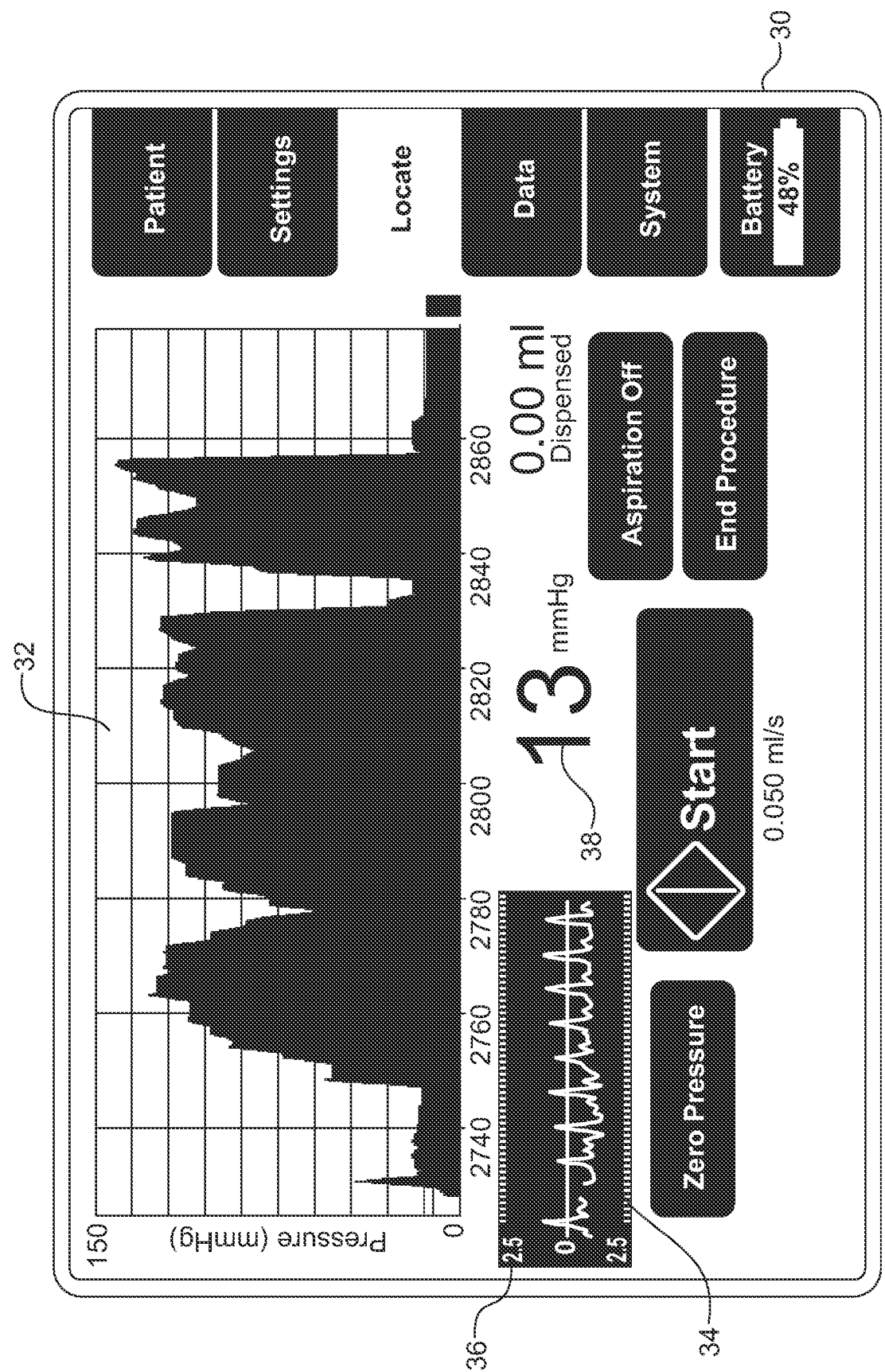
FIG. 4A is a view of a display screen of the system illustrated in FIG. 1 showing fluid pressure measurements detected by the system.
Figure 4B:
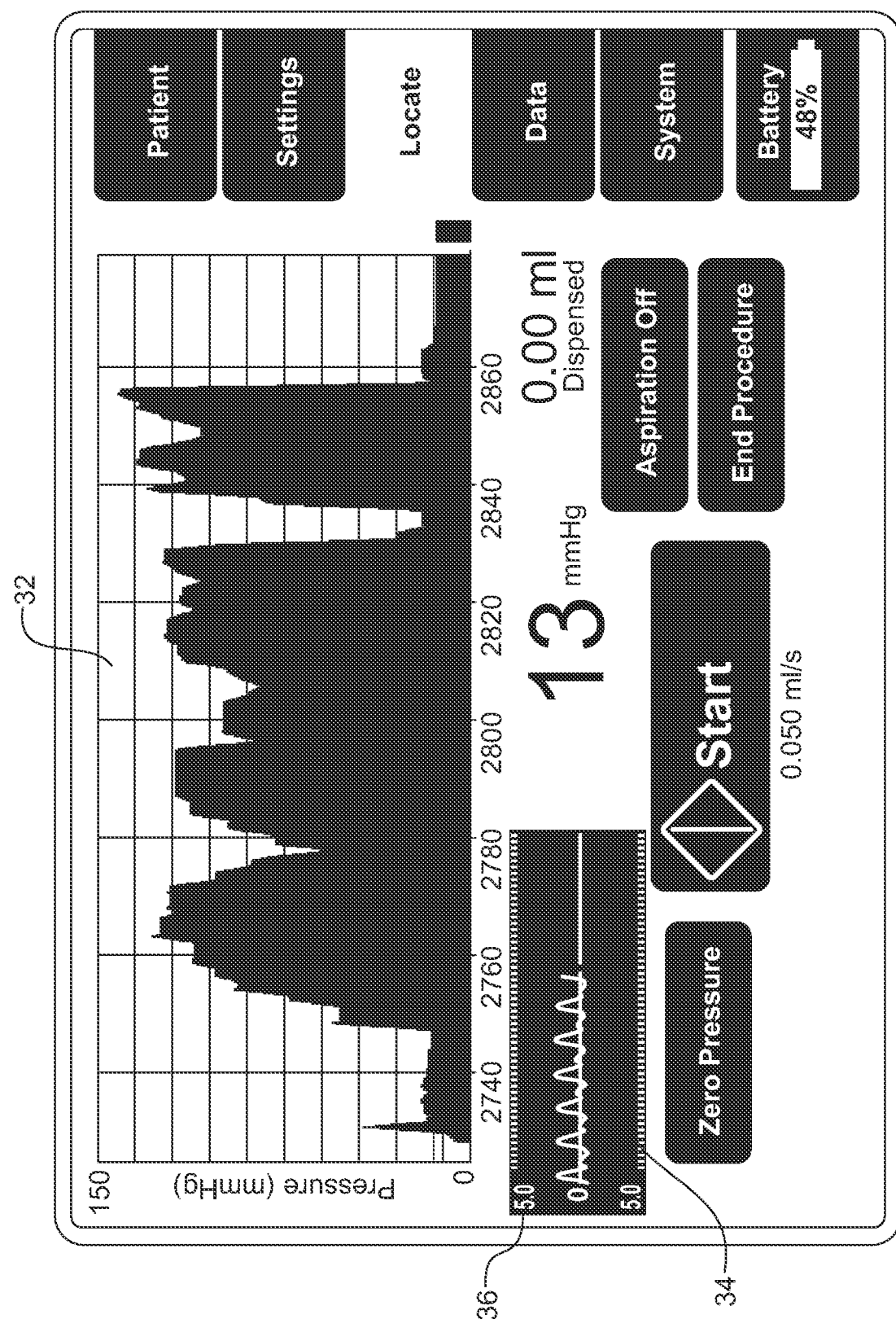
FIG. 4B is a view of a display screen of FIG. 4A illustrated with a different amplitude range.
Figure 4C:
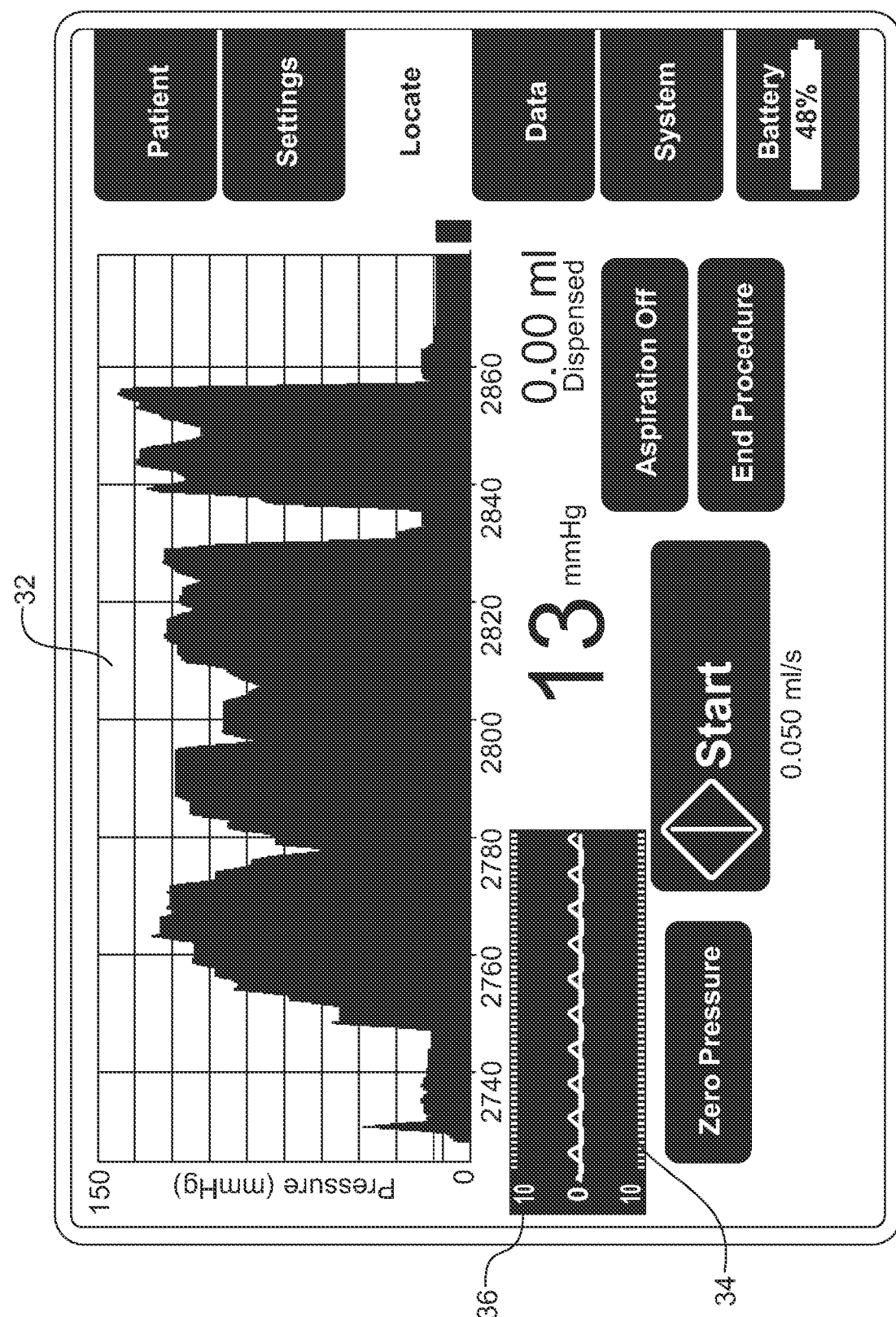
FIG. 4C is a view of a display screen of FIG. 4B illustrated with a different amplitude range.

The system may be configured to provide one or more visual signals for the user to observe and/or analyze the detected pressure signals. For instance, referring to FIGS. 1-4A, the system 10 may include a display screen 30 for displaying data related to the operation of the system, including, but not limited to, pressure data and fluid flow data. For example, as shown in FIGS. 4A-4C the system includes a primary pressure graph 32 on the display 30. The primary pressure graph 32 plots the fluid pressure against time so that the graph represents the variations in detected fluid pressure over a period of time. This graph represents general pressure trend information and in the present instance the controller processes the signal received from the pressure detection element to remove variations that are not created by fluid pressure. For example, the controller 30 may be programmed to process the pressure data to remove variations of pressure signals caused by motor operation, syringe stiction, and general pressure variations caused by flexing of the tubing and needle tip elevation changes. Higher frequency variations and noise are removed through the use of a low pass filter of either an electrical or software implementation. As shown in FIGS. 1 and 2, the display may also include a current pressure display 38 that displays the most recently detected fluid pressure.

Additionally, the display 30 also includes a pulsation wave detection display 34. As discussed below, it may be desirable to analyze the fluid pressure data to detect the presence of a pulsatile waveform. The controller is configured to process the data in a manner that isolates a pulsatile wave from the underlying fluid pressure in the environment of the needle as described below. The pulsation wave display 34 shows this processed data so that the operator can determine whether the data is indicative of the presence of a pulsatile waveform. As discussed below, the pulsation wave display 34 includes an amplitude range identified as element 36. This amplitude range 36 can be varied in order to more clearly display the pulsatile wave form depending on the amplitude of the waveform.

As noted above, it may be desirable to analyze the fluid pressure data to detect the presence of a pulsatile waveform in the pressure data detected by a pressure sensor, such as sensor 20. In fluid dynamics, a flow with periodic variations is known as pulsatile flow. Pulsatile flow is an intrinsic property of the cardiovascular system. In other words, the basic operation of the cardiovascular system generates pulsatile flow as follows: when the ventricle contracts and creates the needed pressure gradient, a volume of blood is rapidly ejected into the arterial vessels. The aorta and arteries have a lower resistance to blood flow compared to smaller blood vessels, such as arterioles and capillaries. Due to the slower outflow to the arteriole, the arteries are inflated to accommodate the extra blood volume. During diastole, the elastic recoil of the arteries forces the blood out into the arterioles. In this way, the elasticity of the arteries helps to convert the pulsatile flow of blood from the heart into a more continuous flow through the rest of the circulation.

The pulsatile waveform produced intravascularly by the cardiovascular system also creates a corresponding extravascular pulsatile waveform cause by movement of blood vessels, such as arteries. For instance, arteries in the nerve bundle in the spinal cord create a pulsatile waveform that is observed in the spinal fluid in the epidural space. The frequency of the extravascular pulsatile waveform is similar to the intravascular pulsatile waveform; however, the magnitude of the extravascular waveform is significantly lower than the magnitude of the intravascular pulsatile waveform. Specifically, the intravascular pulsatile waveform is created directly by the blood pressure whereas the extravascular pulsatile waveform is created by movement of blood vessels in response to the blood pressure.

In order to identify pulsatile waveform, the data may be processed to isolate the data representative of the pulsatile waveform. The pulsatile waveform may be difficult to identify due to the magnitude of the background fluid pressure. For instance, the amplitude of the pulsatile waveform may by an order of magnitude lower than the background fluid pressure. For example, if the needle is located in dense tissue the detected fluid pressure may exceed 100 mmHg, whereas the amplitude of the pressure variations resulting from the pulsatile wave may be only 10 mmHg. In such an instance, the pressure may only fluctuate from 95 mmHg to 105 mmHg, which may be imperceptible on a plot of pressure versus time. Therefore, it is desirable to isolate the pressure of the pulsatile wave from the underlying pressure, wherein the underlying pressure or background pressure is the pressure that results primarily from the density of the tissue in which the tip of the needle is located.

To isolate the data representative of a pulsatile wave, the controller may include a self-centering filter to maintain the waveform at the center of the graph of pulsation wave detection display 34. Various filter types may be implemented to remove the average value. These filters may be constructed using mechanical, electrical or software designs. In the present instance, a running average filter is designed into software programmed into the controller to generate an average value for pressure which is subtracted from the current pressure reading for graphing purposes. This maintains the pulsation waveform data centered on the graph. For example, the data may be processed so that the data is generally centered on a base line between the upper limit of the pulsatile waveform and the lower limit of the pulsatile waveform. In one embodiment, the pressure data may be processed as follows: first, an average pressure value is calculated based on the pressure values detected by the sensor during the most recent time period, such as a time period varying between 2 and 10 seconds. The calculated average is then subtracted from the current pressure value. The system displays the resulting value on the pulsation detection display 34. Large transient pressures will cause the plotting to be clipped on the pulsation detection display 34, however, the average will settle to the center of the detection display 34.

Figure 4D:
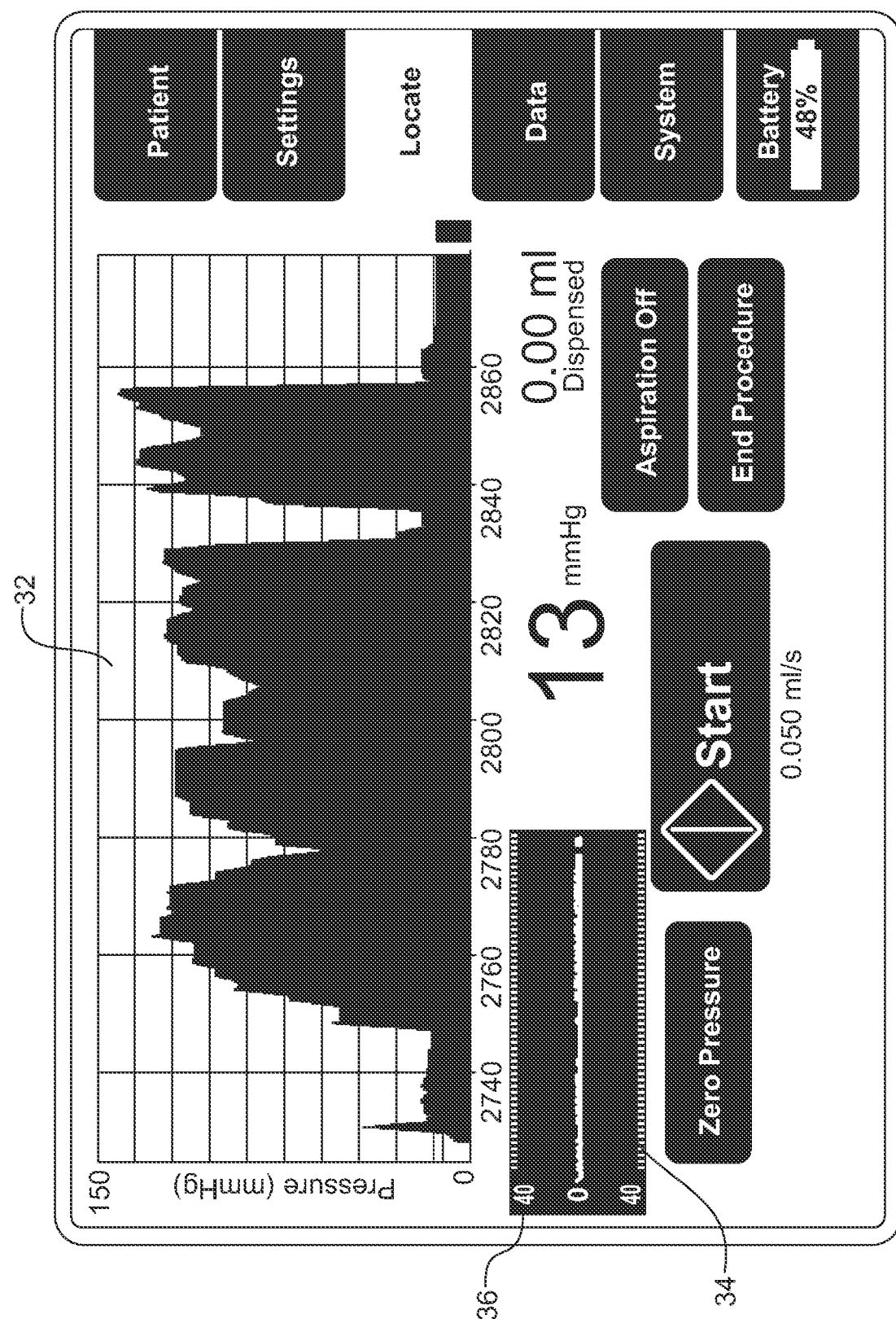
FIG. 4D is a view of a display screen of FIG. 4C illustrated with a different amplitude range.

The amplitude of the pulsatile waveform may vary from situation to situation. Additionally, the fluid pressure at which the pulsatile waveform becomes noticeable may also vary. As described above, the controller may be configured to process the data from the pressure sensor to isolate the pulsatile waveform. Additionally, the controller may be configured to process the data from the pressure sensor to attempt to center the waveform on the pulsation detection display 34. Although the process of attempting to center the waveform may improve the likelihood of identifying the pulsatile waveform, it is still possible to overlook the waveform in many situations. For instance, FIGS. 4A-4D display how scaling the amplitude of the pulsation detection display can determine whether the pulsatile motion is detected. Specifically, in FIG. 4A the display illustrates the processed pressure data with an amplitude scaling of 5 mm Hg (2.5 above the base line and 2.5 below the baseline). As can be seen in FIG. 4A, the pulsatile waveform is readily identified using this scaling. Referring to FIG. 4B, the amplitude range 36 is twice that of FIG. 4A. As such, the oscillations are significantly diminished but still noticeable. In FIG. 4C the amplitude range is doubled again. The oscillations are subtle but possible to identify. In FIG. 4D the amplitude range is doubled again. In the scale of FIG. 4D the pulsatile waveform is not discernible. Accordingly, if the operator were to start with a large amplitude range 36 as in FIG. 4D it would seem that the sensor 20 did not detect a pulsatile waveform.

Figure 5A:
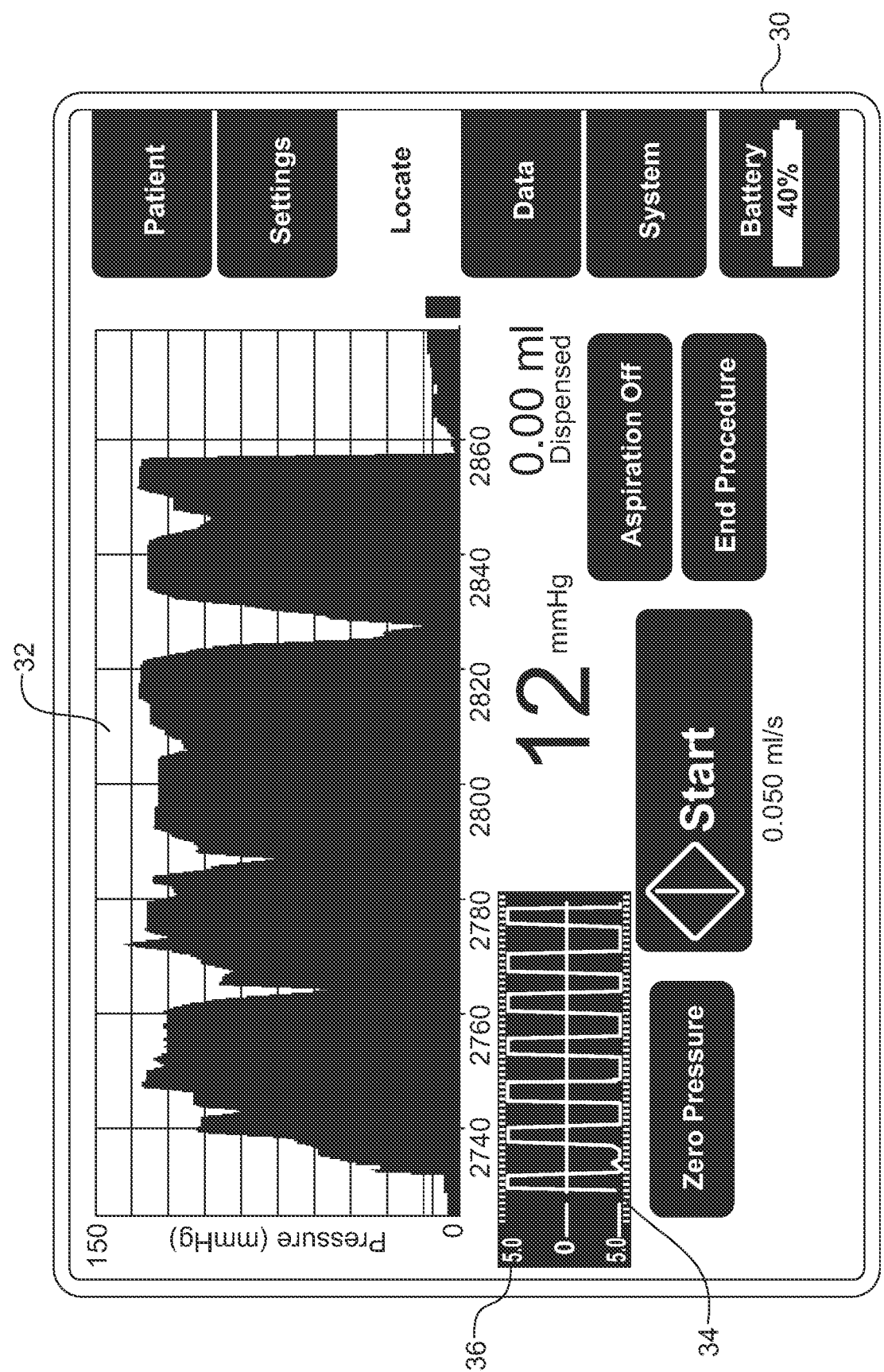
FIG. 5A is view of the display screen of the system illustrated in FIG. 1.
Figure 5B:
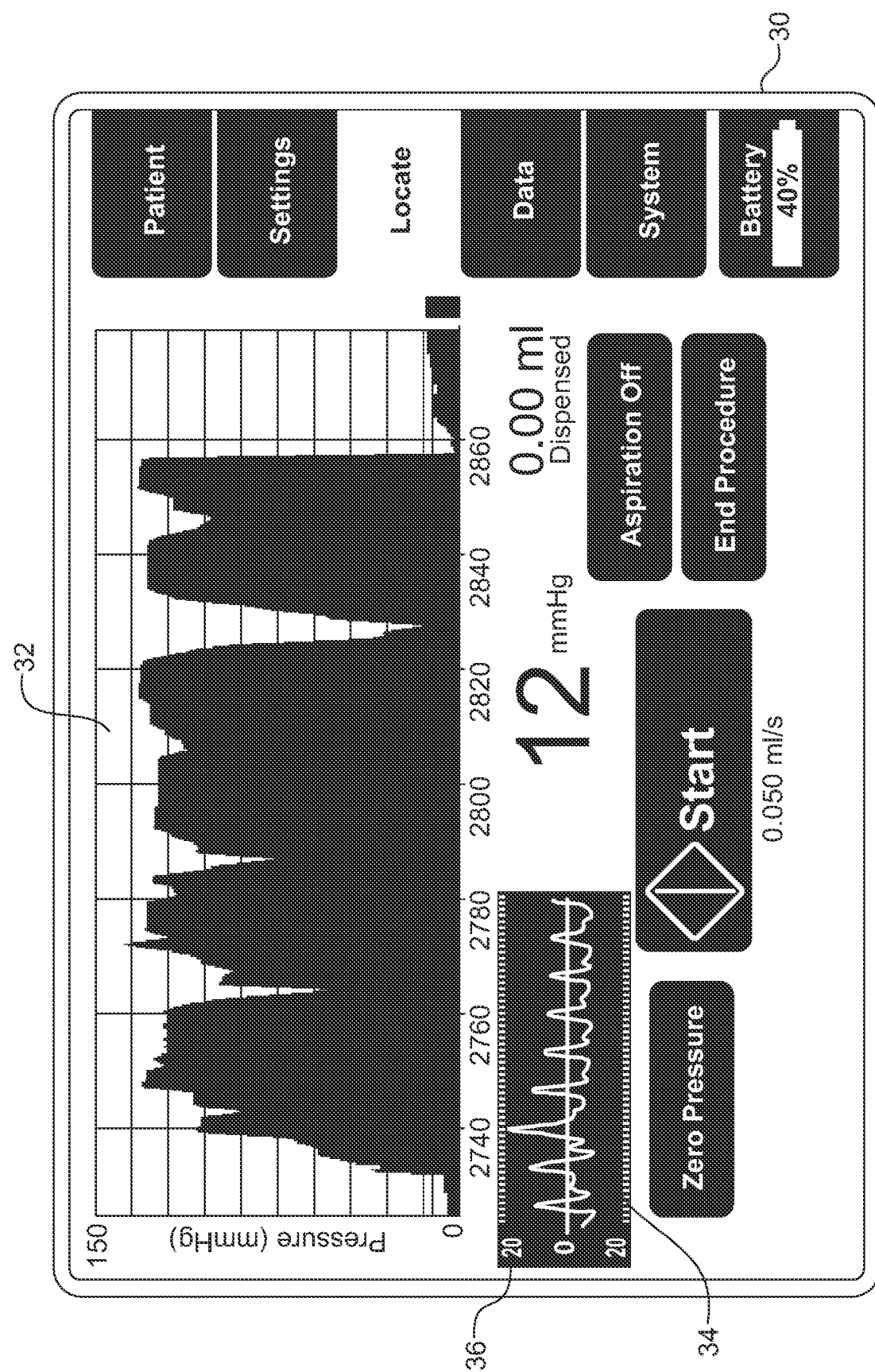
FIG. 5B is a view of the display screen shown in FIG. 5A illustrated with a different amplitude range.

In contrast, FIGS. 5A and 5B illustrate the opposite problem. In FIG. 5A the data is plotted with an amplitude range 36 of 10 mm Hg. However, the range of the pressure data is greater than 10 mm Hg so many of the data points are off the scale. Referring to FIG. 5B, the same data is plotted with an amplitude range of 40 mm Hg. Since the amplitude range is large enough to fit all of the pressure data, the pulsatile waveform is identifiable on FIG. 5B.

Since the amplitude range for a given set of pressure data is highly variable, the system may include the option of easily scaling the date to change the amplitude range. Specifically, the system 10 includes the ability to readily re-graph the processed pressure data in response to the operator selecting or inputting a change in the amplitude range. The request may be input using any of a number of input mechanisms, including but not limited to a mouse, a footswitch, voice activation, a keyboard, a button on the drive unit 50 or a touch screen button, as well as, automatically rotating through different amplitude ranges via the software. In the present instance, the display 30 is a touchscreen that the touchscreen includes a button that allows the operator to toggle though any in a variety of amplitude ranges. When the user selects a different amplitude range, the system re-graphs the data. In this way, the operator can manipulate the display of the pressure data to identify whether a pulsatile waveform is present.

Noise Compensation

As discussed above, the system 10 may be configured to continue to inject fluid through the needle while the system or the operator analyzes the pressure data to detect the presence of a pulsatile waveform. However, the injection of fluid may cause disturbances that affect detection of the pulsatile waveform. For instance, the turbulence from the fluid flow and the stiction of the rubber/elastomeric piston in the syringe are two variables that can adversely affect the detection of the pulsatile waveform. To overcome the potential issues created by such disturbances, the system may be configured to isolate the pulsatile waveform from the effects of the disturbances.

To isolate the pulsatile waveform, the system may include a process for assessing the disturbances that are caused by the configuration of the system and the injection of fluid. In a particular embodiment, the system includes a noise cancellation mode. Prior to inserting the needle into the patient, the user selects the noise cancellation mode. The system then runs the drive unit to inject fluid through the needle. The system monitors any changes in pressure that arise during the noise cancellation mode. When assessing the presence of a pulsatile waveform, the system modifies the detected pressure data based on the data collected during the noise cancellation mode.

System Control

The system includes a user operable input mechanism, which allows the operator to provide input signals for controlling the system. The input mechanism may be any of a variety of devices, such as a touch screen, buttons on the drive unit or a foot-operated control that provides a means for the operator to start, stop, and change the flow-rate from a single flow-rate to a second or third distinct pre-set flow rate. Alternatively, the input element may be a mouse, keyboard or a microphone for providing input commands audibly. Additionally, the system may include a plurality of input mechanisms to allow the operator to input a variety of inputs for various stages of a procedure. For example, the system may include a first input mechanism, such as a foot pedal that controls the flow of fluid through the device. Actuating the foot pedal switch (i.e. depressing the switch) sends a signal to the CPU of the drive unit, which in turn sends a signal to the motor to drive the motor so that fluid flows from the syringe to the needle 24 as long as the pedal is actuated. Alternatively, actuating the foot pedal a first time may operate a start signal to start the fluid flow and the fluid may continue to flow until the operator actuates the foot pedal again. In this way, the second actuation operates as a stop signal to discontinue the fluid flow.

As described above, the system is operable to control the flow of fluid during a procedure. In addition to using an actuator to control on/off, the system may provide two or more flow rate settings. In particular, the control unit 50 may incorporate a multi-speed pump that provides a variable flow rate. Similarly, the pump may include two or more pre-set flow rates. In the present instance, the control unit 50 includes an electric motor 70 that controls the speed at which the control unit displaces the plunger in the syringe 18. The control unit 50 may control the speed of the motor 70 so that the motor is driven at one of multiple pre-set speeds to provide multiple pre-set flow rates. The different flow rates can be used in conjunction with different pressure settings and/or other characteristics during different portions of a procedure.

The switch between pre-sets can be manual or automatic. For example, the operator may manipulate an input device, such as a keyboard, touch pad, or otherwise, as noted above. Alternatively, the system may automatically switch to the second pre-set based on detected criteria, such as the fluid pressure.

Method of Operation

An exemplary method for guiding a needle to a target location using the system described above will now be described. It should be understood that the present system is not limited to use in guiding a needle for infusion of a medicament. Accordingly, it should be understood that the principles and methods described below may be readily adapted for the insertion of a needle into tissues and anatomical areas in a variety of applications and procedures.

When the needle is adjacent fluid or a vessel producing a pulsatile waveform, the processed pressure data forms an oscillatory wave, such as a sinusoidal wave. Detection of the pulsatile waveform can act as a primary indication that the needle is positioned at or adjacent the target tissue. Alternatively, detection of the pulsatile waveform can operate as a validation or verification that an alternate method for identifying a target tissue (such as by a loss-of-resistance technique) was accurate. In this way, the detection of a pulsatile waveform can operate in combination with another search methodology in order to increase the likelihood of proper needle placement and reduce the likelihood of inadvertent needle/anesthesia injuries. In the following example, the system is used in combination with a loss-of-resistance technique for identifying a target tissue.

First, the operator determines that the target tissue is one in which the target tissue will generate a pulsatile waveform. After making or confirming such a determination, the operator advances the needle 24 into the patient, preferably as fluid flows through the needle at a set flow rate. In a method in which the drive unit is utilized, fluid reservoir, such as a syringe, is loaded into the drive unit 50. The drive unit then precisely controls the position of the drive element 58 to precisely control the flow of fluid from the syringe. The pressure sensor 20 detects the fluid pressure at the needle and as shown in FIG. 4A, the fluid pressure varies as the needle is advanced through different tissue types. When searching for a target tissue, the change in fluid pressure may guide the advancement of the needle. For example, the system may provide a perceptible output that guides the operator. In one example, the system may provide an audible tone representative of the pressure. For instance, the pitch of the audible signal may increase as the pressure increases and may decrease as the pressure decreases. Similarly, the system may provide a visual signal indicative of the change in pressure. For instance, as illustrated in FIG. 4A a graph 32 provides a visual indication of the fluid pressure. The graph 32 plots the pressure as it varies over time. In FIG. 4A, an apparent loss of resistance appears to occur at an approximate time of 2840 seconds. However, a true loss of resistance occurs at an approximate time of 2860 seconds. The present system can be used to confirm when an apparent loss of resistance is an actual loss of resistance as discussed further below.

As noted above, when the needle 24 is being advanced or withdrawn the fluid pressure changes as the needle passes through different tissue types. Conversely, when the needle is maintained at a particular location the fluid pressure will tend to stabilize and hold at a generally constant value. However, if the needle tip is maintained in a substantially constant location the sensor may detect pressure variations due to a pulsatile wave. Specifically, if the needle is maintained in a particular location relative to a target area and if the particular location is adjacent an artery then the system will detect periodic variations in the detected fluid pressure. Furthermore, the detected magnitude of the fluid pressure may also guide the user in addition to the detection of periodic variations. For example, if the system detects a pressure profile having periodic pressure variations then the needle may be adjacent an artery. However, if the fluid pressure is elevated and the amplitude of the pressure variation is above a threshold then the system may determine that the needle is within the artery rather than next to the artery. For instance, a pressure curve that indicates periodic variations between 80 mm/Hg to 120 mm/Hg would be indicative of the needle being within an artery rather than next to the artery.

In this way, the system may combine the detection of periodic variations in the fluid pressure with a second fluid pressure characteristic, such as loss of resistance as described above. For example, the system may monitor the fluid pressure as the operator advances the needle to guide the operator toward a target tissue, such as the epidural space. Once the system detects a drop-in pressure indicative of a loss of resistance, the system may indicate that the needle is in the epidural space. In response to this determination, the system provides a signal to the user indicating that the needle is located at the target tissue so that the user maintains the needle in the particular location. To verify that the needle is in the epidural space, the system may monitor the fluid pressure to determine the presence of periodic variations in the detected fluid pressure. If the system detects periodic variations in the fluid pressure indicative of a pulsatile waveform, then such detection is validation that that the needle is located in the epidural space. Having validated that the needle is either adjacent to, or located within, the target tissue, the medicament can be safely injected through the needle and into the patient at the target tissue site.

It should be understood that in the foregoing description the system is described as automatically detecting the presence of a pulsatile waveform to validate the determination of the needle placement. However, it should be understood that in addition to the system 10 being configured to automatically detect the presence of a pulsatile waveform, alternatively, the system may be configured to display the fluid pressure data in a way that facilitates the operator determining that the needle is detecting a pulsatile waveform.

In the foregoing method, an operator locates a needle adjacent a target tissue by utilizing constant feedback regarding the fluid pressure detected at the needle to guide the needle. One such method for guiding the needle is a loss of resistance process for identifying a target tissue site that is adjacent a dense barrier tissue. Once the barrier tissue is penetrated the fluid pressure drops rapidly, providing an indication that the needle is properly positioned in the target space. The system then validates the needle placement for processing the pressure data to attempt to detect a pulsatile wave. The detection of the pulsatile wave operates as a validation of the needle placement.

Although the foregoing example illustrates the use of the system in connection with a loss of resistance process for positioning a needle in a particular location, it should be understood that any number of processes can be used to place the needle at the target site, so long as the target site is adjacent tissue that is likely to provide a pulsatile waveform. For instance, as described below, the system may operate in combination with a peripheral nerve block system to verify or validate that the needle is properly placed.

In a peripheral nerve block process, the target tissue are nerves associated with a neurovascular bundle. When an anesthetic is injected adjacent to the nerve then the anesthetic can provide appropriate anesthesia. However, if the needle is placed within the nerve then the anesthetic can cause damage to the nerve. Accordingly, a peripheral nerve block process may use electrical stimulation to guide the needle. The level of the stimulation can be varied to guide the needle toward the target site. The operator advances the needle and applies an electrical stimulation to the tissue at the tip of the needle. If a response to the electrical stimulation is noted, then the needle may be adjacent the target nerve. Furthermore, as described in International Patent Application No. PCT/US18/31096 published as Publication No. WO 2018/204789 on Nov. 8, 2018 the fluid pressure adjacent the needle tip can be monitored during a peripheral nerve block procedure. The entire disclosure International Patent Application No. PCT/US18/31096 published as Publication No. WO 2018/204789 is hereby incorporated herein by reference. In such a process, the combination of fluid pressure and electrical stimulation can be used to guide the needle to the target site. Once the peripheral nerve block process is used to place the position the needle tip at the target site, the pulsatile wave detection is then used to verify or validate the needle placement. In particular, once the needle is positioned at the proposed location, the positioned of the needle is maintained without significant movement. While the needle is held in position, the system continues to monitor the pressure signal from the sensor 20. The pressure date is processed to isolate the pressure data from the background pressure to identify the presence of a pulsatile waveform. If such a pulsatile waveform is present, then the needle location decision is verified. The operator then performs the next step to the target tissue. The next step may be a medical procedure to the target tissue or the next step may be the injection of a medicament or anesthesia. Alternatively, if the peripheral nerve block procedure positions the needle at a location that is thought to be the target tissue, but a pulsatile waveform is not detected, then the operator determines that the needle is not properly positioned adjacent the target tissue and the process for locating the needle is re-started.

From the foregoing, it should be understood that the present invention may incorporate one or more of a variety of search techniques that are configured to identify or validate that a needle is positioned at or within a target tissue. For instance, in the following discussion the system is used to validate the placement of a needle. However, it should be understood that the system can be used to verify or validate the placement of a conduit other than a needle. One example is the placement of a catheter. Frequently a catheter may be inserted using any of a variety of techniques, such as the loss-of-resistance technique described above. Once the needle is properly placed, a catheter may be inserted into the patient so that the catheter is located at or within the target tissue. The catheter may need to remain positioned within the patient for an extended period. During the extended period of time, the catheter may be moved, thereby accidentally moving the catheter away from the target tissue. Currently the method for verifying the placement of the catheter is to inject a fluid, such as a medicament, and monitor the patient to determine if the medicament had the intended affect. If the medicament affected the patient in the intended manner, then it is determined that the catheter is properly placed; if not the search is re-started. However, the present system can be used to verify or validate the placement of a catheter. Rather than a needle 24, the system may include a hub configured to form a fluid-tight seal with the hub of the catheter. The hub of the system is interconnected with the hub of the catheter to form a fluid-tight seal. The drive unit is then started to inject fluid from the syringe into hub and then into the catheter until the catheter is substantially full of fluid. The system then detects the fluid in the catheter. If the pressure signal includes a pulsatile waveform the operator verifies or validates that the catheter is still properly placed so that fluid can be injected to the target tissue through the catheter. Conversely, if a pulsatile waveform is not detected through the catheter, then the operator determines that the catheter is not properly placed and the catheter can be repositioned.

In the foregoing examples, the pulsatile wave detection is used as a signal to validate or verify a needle or other conduit after the conduit is placed. Additionally, it should be noted that the pulsatile waveform detection can be used as the primary data for guiding the placement of a needle or other conduit. According to one example, a needle is inserted into a patient toward a target tissue. As the needle is advanced toward the target tissue, the amplitude of the pulsatile waveform may increase. Accordingly, by first monitoring for the presence of a pulsatile waveform, the operator determines that the needle is within the general area of the target tissue. As the needle is moved closer to the target tissue, the amplitude of the pulsatile waveform increases. In this way, the variation of the pulsatile waveform is used to guide the needle toward the target tissue.

In particular, the system may be configured to provide guidance for placing a needle or other conduit based on two characteristics. The first characteristic is a pressure range determined by the resistance of the tissue to a constant flow-rate thus producing a first characteristic response to said flow-rate. In other words, a constant flow of fluid is injected through a needle and a sensor detects the pressure range of the fluid in the needle while the needle is in a particular tissue. A second characteristic is determined based on pressure data received by the sensor while the needle is held in a stationary position without fluid being injected through the needle from a fluid reservoir. The second characteristic is based on the presence of a pulsatile waveform. In particular, the second characteristic may be the amplitude of the pulsatile waveform. The system is configured to allow the operator to alternate between a) translational motion of the needle during needle insertion during which fluid flows through the needle and b) stationary positioning of the needle without fluid flow. A comparison of the amplitude of the pulsatile pressure waveform between two or more different locations provides the relative distance of the needle tip to the target. When translation of the needle is stopped so that the needle is maintained at a stationary position, the second characteristic is noted again. The comparison of the height of the amplitude of the pulsatile waveform between two or more time points may be aided by modifying and varying the scale 36 of the pulsatile pressure waveform graph 34 to enable visualization of the height of amplitude of the oscillating waveform. Comparing the amplitude height of the pressure waveform between two or more different time points provides information for determining the relative position of the needle tip to the target tissue. For example, if the amplitude of the subsequent pressure waveform is decreasing compared to the prior waveform then the needle is moving away from the target tissue. Conversely if the amplitude of the subsequent pressure waveform is increasing compared to the prior waveform then the needle is moving toward the target. And, if the amplitude of the pressure waveform does not significantly change between two time points then the relative distance of the needle tip to the target tissue has not changed. It is understood, that the apparatus is capable of varying the amplitude scale to the identify pressure waveforms of varying intensity during this process. Thus, the reliance of a first characteristic to identify a specific space or tissue and subsequent use of a secondary characteristic with varying amplitude provides objective data as to the directional movement of the needle within the tissues and forms the basis for using these two different characteristics to determine guidance of the needle to the target tissue.

One example of using the amplitude of the pulsatile waveform as feedback for a needle placement procedure is a dental application. The method includes setting a specific scale for the pulsatile wave graph 34 and observing the amplitude of the pulsatile waveform from the center of the graph 34 at a given distance. As the operator advances the needle closer to the intended target an increase in the amplitude is noted during the intermittent stopping of needle advancement and injection of drug. This provides guidance to the movement of the needle tip thus enabling the anesthetic solution to be deposited close the neurovascular bundle of the Inferior Alveolar Nerve Plexus. This system is used in conjunction with the dental instrument with a LED screen displaying a pulsatile waveform graph, such as display 34. Additionally, rather than using an in-line single use sensor, the system can incorporate a re-useable sensor that is not in-line. For example, the injection assembly may include a fluid line having a flexible side wall. A clam shell shaped sensor engages the outer wall of the tubing so that the flexible side wall is between the halves of the clam shell sensor. The sensor detects the radial pressure of the fluid pressing radially outwardly, which is indicative of the fluid pressure in the tube and consequently the fluid pressure within the needle. In this way, the claim shell sensor functions as an alternative to an in-line pressure sensor currently described for the epidural system. The clam-shell piezo-electric sensor allows the tubing to be placed within the clam-shell to detect the in-line fluid pressure.

The system 10 can also be incorporated into a process for placing a needle or other conduit to confirm placement of a spinal needle into cerebrospinal fluid. The system may be used in combination with a loss-of-resistance technique previously discussed to guide the needle into the appropriate position and then the needle will be stopped at the determined position. The system the processes the fluid pressure data while the needle movement is stopped. If a pulsatile waveform is detected, then the operator determines that the needle is properly placed in the cerebrospinal fluid.

Further still, the system can be incorporated into other procedures to identify whether a needle or other element is properly placed. One such application is a cardiac-vascular application. In a cardiac-vascular application the system is used to determine the placement of a needle or catheter into the lumen of a vessel by measuring the absolute pressure in addition to detecting the presence of a pulsatile waveform to determine the patency of the vessel during placement of a vascular stent and/or during the use of cardiac ablation in which a therapeutic drug or diagnostic procedure is performed to determine the patency of said vessel of the cardio-vascular system. Detection of a pulsatile waveform in conjunction with the absolute pressure values provides diagnostic information when performing these procedures.

Yet another application of the system 10 is directed to an infusion pump. In the embodiments described above, the system utilizes a syringe pump to insert fluid into the patient. However, the present improvements may be embedded for use in an infusion pump system which includes a peristaltic pump system with a closed drug delivery system consisting of a drive unit, tubing, and an indwelling catheter in a patient's vein. The system would operate by intermittently stopping the motor to enable the detection of a pulsatile waveform to confirm that the catheter has not migrated from the position in the patient. In this way, the system provides a process for determining the position of the catheter and its relative patency during use.

It will be recognized by those skilled in the art that changes or modifications may be made to the above-described embodiments without departing from the broad inventive concepts of the invention. For instance, in the foregoing description, the system is described in the context of providing fluid infusion. However, it should be understood that the system may be used for placement of a needle to aspirate fluid-filled tissue or sample a target tissue such as performing a biopsy. It should therefore be understood that this invention is not limited to the particular embodiments described herein but is intended to include all changes and modifications that are within the scope and spirit of the invention as set forth in the claims.

We claim:

1. A needle-bearing dental instrument for administering a fluid into target location for use in dental treatment of a subject, comprising:
   a fluid reservoir for storing the fluid to be provided to a needle;
   an ejection element displaceable relative to the fluid reservoir to expel fluid from the reservoir;
   a drive element configured to engage the ejection element to control displacement of the ejection element;
   a sensor for detecting a pulsatile pressure waveform in the fluid in the needle, wherein the sensor is configured to continuously detect as the needle-bearing dental instrument is inserted into the subject;
   a controller operable to control the drive element to control the flow of fluid from the reservoir to the needle, the controller configured to periodically discontinue movement of the drive element and process data from the sensor to detect one or more characteristic indicative of the pulsatile waveform; and
   a conduit in fluid communication with the fluid reservoir and the needle.

2. The instrument of claim 1, wherein the sensor is an in-line fluid pressure sensor in fluid communication with the needle.

3. The instrument of claim 1, wherein the conduit is disposed within the sensor.

4. The instrument of claim 3, wherein the sensor comprises a clam shell shape and is disposed around the conduit.

5. The instrument of claim 3, wherein the sensor is configured to detect a pressure of the fluid pressing radially outwardly on a flexible sidewall of the conduit, the detected pressure indicative of the fluid pressure in the conduit and consequently the fluid pressure within the needle.

6. The instrument of claim 3, wherein the sensor comprises a piezo-electric sensor.

7. A method for depositing an anesthetic solution to the neurovascular bundle of the inferior alveolar nerve plexus, comprising: providing the needle-bearing dental instrument of claim 1; providing the fluid, in the form of an anesthetic solution, to the fluid reservoir; and operating the needle-bearing dental instrument to deliver the anesthetic solution to the neurovascular bundle of the inferior alveolar nerve plexus.

* * * * *